(12) United States Patent
Beal

(10) Patent No.: US 9,592,212 B2
(45) Date of Patent: Mar. 14, 2017

(54) USE OF PAN-PPAR AGONISTS FOR TREATMENT OF TAUOPATHIES

(71) Applicant: Cornell University, Ithaca, NY (US)

(72) Inventor: Flint Beal, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/274,025

(22) Filed: May 9, 2014

(65) Prior Publication Data

US 2014/0350107 A1 Nov. 27, 2014

Related U.S. Application Data

(63) Continuation of application No. PCT/US2012/064410, filed on Nov. 9, 2012.

(60) Provisional application No. 61/557,729, filed on Nov. 9, 2011.

(51) Int. Cl.
| | | |
|---|---|---|
| *A61K 31/195* | (2006.01) | |
| *A61K 31/19* | (2006.01) | |
| *A61K 45/06* | (2006.01) | |
| *A61K 31/192* | (2006.01) | |

(52) U.S. Cl.
CPC ............ *A61K 31/195* (2013.01); *A61K 45/06* (2013.01); *A61K 31/192* (2013.01)

(58) Field of Classification Search
CPC .... A61K 31/19; A61K 31/192; A61K 31/216; A61K 31/195
USPC .................................................. 514/557, 563
See application file for complete search history.

(56) References Cited

U.S. PATENT DOCUMENTS

| | | |
|---|---|---|
| 2002/0055529 A1 | 5/2002 | Bisgaier et al. |
| 2004/0092596 A1 | 5/2004 | Adams et al. |
| 2005/0037102 A1 | 2/2005 | Tan et al. |
| 2007/0299047 A1 | 12/2007 | Maher et al. |
| 2009/0143279 A1 | 6/2009 | Mootha et al. |

FOREIGN PATENT DOCUMENTS

WO    WO 2006119329 A2 * 11/2006   ............. A61K 31/00

OTHER PUBLICATIONS

Kreister et al., "Lipid-lowering drugs in the MPTP mouse model of Parkinson's disease: Fenofibrate has a neuroprotective effect, whereas bezafibrate and HMG-CoA reductase inhibitors do not", Brain Research, vol. 1135, No. 1, pp. 77-84 (Mar. 2007).*
Johri et al., "Pharmacologic Activation of Mitochondrial Biogenesis Exerts Widespread Beneficial Effects in a Transgenic Mouse Model of Huntington's Disease," 2012, Human Molecular Genetics, 21(5):1124-1137.
International Search Report for PCT/US2012/064410 mailed Mar. 14, 2014 (3 pages).

* cited by examiner

*Primary Examiner* — Kevin E Weddington
(74) *Attorney, Agent, or Firm* — Sutherland Asbill & Brennan LLP

(57) ABSTRACT

The present invention provides a therapeutic treatment for a neurodegenerative disease with a pan-PPAR agonist, such as bezafibrate. In particular, the present invention provides that pan-PPAR agonists enhance PPAR related responses in both the central nervous system and peripheral tissues in Huntington's Disease (HD) and tauopathy. Therapeutic compositions comprising one or more pan-PPAR agonist(s), and kit thereof, for treating a neurodegenerative disease or disorder are also provided.

9 Claims, 18 Drawing Sheets

FIGURE 3A                                   FIGURE 3B

USE OF PAN-PPAR AGONISTS FOR TREATMENT OF TAUOPATHIES

CROSS REFERENCES TO RELATED APPLICATIONS

This application is a continuation of PCT Application No. PCT/US2012/064410 which claims priority to U.S. Provisional Application No. 61/557,729, filed Nov. 9, 2011, the entire contents of which are incorporated by reference herewith.

GOVERNMENT FUNDING

This invention was made with Government support under Grant Numbers P01AG14930 and AG014930 awarded by the National Institutes of Health. The United States Government has certain rights in the invention.

BACKGROUND OF THE INVENTION

Peroxisome proliferator-activated receptors (PPARs) are a group of nuclear receptor proteins that act as ligand-dependent transcription factors (Kersten et al 2000). PPARs are also ligand-inducible transcription factors belonging to the steroid, thyroid and retinoid receptor superfamily and also termed nuclear hormone receptors (Desvergne and Wahli 1999; Straus and Glass 2001). Nuclear receptors directly bind to DNA and regulate gene expression through transcriptional co-activation (Nolte et al. 1998; Berger and Moller 2002; Castrillo and Tontonoz 2004). The PPAR subfamily is comprised of three isoforms: PPAR-α, PPAR-β/δ and PPAR-γ, and these isoforms share structural homology in various species (Desvergne and Wahli 1999; Bishop-Bailey 2000; Buchan and Hassall 2000; Straus and Glass 2001). PPARα, β, and γ are the three commonly known PPAR isotypes. PPARα is predominantly expressed in the liver, kidney, muscle, adipose, and heart, whereas PPARβ is found in the brain, adipose, and skin, and PPARγ is expressed ubiquitously (Bensinger and Tontonoz 2008). These transcription factors have been linked to lipid transport, metabolism, and inflammation pathways (Bensinger and Tontonoz 2008). Because of this, synthetic PPAR agonists have been generated as therapeutic agents for the treatment of diabetes and metabolic diseases (Schulman 2010; Wang 2010).

PPAR are activated by small, lipophilic compounds and form heterodimers with the retinoid X receptor-a (RXR) in the cytoplasm for full activation (van Neerven and Mey 2007). After activation the PPAR/RXR heterodimer binds to the specific DNA sequence (peroxisome proliferator response element; PPRE) on the promoter region of PPAR target genes (Desvergne and Wahli 1999; Qi et al. 2000) to modulate transcriptional activity. Specific binding of PPAR on DNA sequences leads to activation of hundreds of gene cascades involved in several biological processes (Qi et al. 2000). In the absence of ligands, PPAR and RXR heterodimers bind to co-repressor complexes and suppress gene transcription (Ziouzenkova and Plutzky 2008).

While, binding of PPAR with specific ligands leads to release of co-repressors from heterodimers and recruitment of co-activators, followed by activation of the basal transcriptional machinery (Kamei et al. 1996; Desvergne and Wahli 1999; Straus and Glass 2001), dietary lipids and their metabolites, fatty acids and eicosanoids are the natural ligands for PPAR. However, these receptors are also activated by synthetic ligands such as thiazolidinediones, fibrates, W501516 and L-165041 (Desvergne and Wahli 1999; Straus and Glass 2007). Several non-steroidal anti-inflammatory drugs (NSAIDs), such as ibuprofen, fenoprofen and indomethacin also activate PPARα and PPAR-γ (Lehmann et al. 1997). It was postulated that the anti-inflammatory actions of these drugs may arise from their ability to bind to PPAR, and subsequent activation of these receptors (Jiang et al. 1998; Ricote et al. 1998; Casper et al. 2000; Heneka and Landreth 2007).

Different PPAR isoforms develop from a common PPAR gene and show tissue dependent patterns of expression during fetal development and are involved in differentiation of adipose tissue, brain, skin, liver, muscle and placenta (Desvergne and Wahli 1999; Gofflot et al. 2007). On the basis of target genes and differential localization in the tissues, these isoforms perform different pharmacological, physiological and biological functions and exhibit different ligand specificities (Desvergne and Wahli 1999). PPAR-α is activated by natural fatty acids and synthetic fibrate ligands and regulates metabolism of lipid and apolipoproteins. PPAR-γ is involved in regulation of adipocyte differentiation (adipogenesis), glucose metabolism, insulin sensitivity and cell growth and is activated by natural ligands as well as synthetic glitazone ligands, while, PPAR-β/δ regulates lipid and glucose metabolism.

PPARs can affect metabolism and inflammation in the central nervous system (Heneka and Landreth 2007), suggesting that they can play a role in the pathogenesis of neurodegenerative diseases. PPAR agonists increase oxidative phosphorylation capacity in mouse and human cells (Bastin et al 2008; Hondares et al 2006; Wenz et al 2010), and enhance mitochondrial biogenesis.

Prior reports have demonstrated beneficial effects of PPARγ agonists, such as thiazolidinediones (TZD, also called glitazones) (Kaundal and Sharma 2010), in models of stroke (Culman et al 2007) and Alzheimer's disease (Heneka et al 2005; Jiang et al 2008; Nicolakakis et al 2008; Nicolakakis and Hamel 2010). Fibrates, such as fenofibrate (Rakhshandehroo 2010), are another class of PPAR agonists (Abourbih et al 2009; Munigoti and Rees 2011; Staels et al 2008) that primarily target the PPARα pathway. Like TZD, fenofibrate has demonstrated promising protective effects in models of neurodegenerative diseases, including Parkinson's disease (Kreisler et al 2010), and brain injury (Chen et al 2007). Interestingly, the neuroprotective effects of PPAR agonists seem to occur through a common mechanism involving the reduction of oxidative stress and inflammation (Heneka et al 2005; Jiang et al 2008; Nicolakakis et al 2008; Nicolakakis and Hamel 2010; Chen et al 2007).

Bezafibrate is a member of the fibrate family that predominantly activates PPARα, but can also act on PPARβ and γ (Tenenbaum et al 2005). It can therefore be considered a pan-PPAR agonist. Recently, the administration of bezafibrate was shown to increase PGC-1α expression, mitochondrial DNA and ATP levels; and to increase life span and delay myopathy in a COX-10 subunit deficient mouse model of mitochondrial myopathy (Wenz et al 2008). Bezafibrate enhances lipid metabolism and oxidative capacity (Tenenbaum et al 2005; Bastin et al 2008). Bezafibrate is an effective cholesterol lowering drug which is used to lower cholesterol and triglycerides and increase high density lipoprotein (HDL).

Huntington's disease (HD), is a fatal, dominantly inherited progressive neurodegenerative disease, caused by an abnormal CAG repeat expansion in the huntingtin (htt) gene. The disease is characterized by progressive motor impairment, personality changes, psychiatric illness and gradual intellectual decline, leading to death 15-20 years after onset (Vonsattel and DiFiglia 1998). Neuropathological analysis shows a preferential and progressive loss of the medium spiny neurons (MSNs) in the striatum, although cortical atrophy and degeneration of other brain regions occur in later stages of the disease (Vonsattel and DiFiglia 1998; Hayden and Kremer 2001; Zuccato et al 2010). Several transgenic mouse models exist that recapitulate the main features of HD, and which have been used for development and testing of new therapeutic interventions. Transgenic mouse models either contain htt N-terminal fragments, usually the first 1 or 2 exons of the human htt gene with the CAG expansion, or the full-length human HD gene with an expanded CAG tract. All these models share features with human HD. The most extensively studied are the R6/2 mice, which express exon-1 of the human htt gene, and which initially show behavioral and motor deficits at 6 weeks after birth. Subsequently, the phenotype of the R6/2 mice develops rapidly manifesting tremor, clasping, weight loss, diabetes, behavioral abnormalities, and reduced life span of 10-13 weeks (Mangiarini et al 1996; Menalled and Chesselet 2002).

Transcriptional dysregulation, protein aggregation, mitochondrial dysfunction and enhanced oxidative stress have been implicated in the disease pathogenesis. A critical role of peroxisome proliferator activated receptor (PPAR)-γ-coactivator 1α (PGC-1α), a transcriptional master co-regulator of mitochondrial biogenesis, metabolism and antioxidant defenses, has been identified in HD. Interest in the role of PGC-1α in HD pathogenesis initially came from studies of PGC-1α knockout mice (PGC-1αKO), that display neurodegeneration in the striatum, which is also the brain region most affected in HD (Lin et al. 2004; Leone et al. 2005). PGC-1α also plays a role in the suppression of oxidative stress, and it induces mitochondrial uncoupling proteins and antioxidant enzymes, including copper/zinc superoxide dismutase (SOD1), manganese SOD (SOD2), and glutathione peroxidase (Gpx-1) (St-Pierre et al 2006). Oxidative damage is a well characterized feature which is documented in plasma of HD patients, HD postmortem brain tissue, and in HD transgenic mice (Browne and Beal 2006; Hersch et al. 2006).

Using striata from human HD patients, striata from HD knock-in mice and the STHdhQ111 cell-based HD model, Cui et al. (Cui et al. 2006) showed marked reductions in mRNA expression of PGC-1α, and interference of mutant htt with the CREB/TAF4 complex was shown to be instrumental in this reduction. Down-regulation of PGC-1α significantly worsened the behavioral and neuropathological abnormalities in a PGC-1α knock-out HD knock-in mouse model (PGC-1αKO/KI). Administration of a lentiviral vector expressing PGC-1α into the striatum of R6/2 mice, was neuroprotective in that it increased the mean neuronal volume of medium spiny neurons (Cui et al. 2006). Caudate nucleus microarray expression data from human HD patients showed significant reductions in 24 out of 26 PGC-1α target genes (Weydt et al 2006). These authors also found reduced PGC-1α mRNA expression in striata of the N171-82Q transgenic mouse model of HD.

Subsequent studies were carried out, which showed that the ability to upregulate PGC-1α in response to an energetic stress, produced by administration of the creatine analogue, guanidinopropionic acid, was markedly impaired in HD transgenic mice (Chaturvedi et al. 2009; Chaturvedi et al. 2010). PGC-1α plays a critical role in mitochondrial biogenesis in muscle, and in influencing whether muscle contains slow-twitch oxidative or fast-twitch glycolytic fibers (Lin et al. 2002). Impaired generation of ATP in muscle and a myopathy occurs in gene-positive individuals at risk for HD, HD patients and HD transgenic mice (Gizatullina et al 2006; Kosinski et al. 2007; Turner et al 2007). Impaired PGC-1α activity was observed in muscle of HD transgenic mice, and in myoblasts and muscle biopsies from HD patients (Chaturvedi et al 2010). A pathologic grade-dependent significant reduction in numbers of mitochondria in striatal spiny neurons, which correlated with reductions in PGC-1α and the mitochondrial transcription factor a (Tfam) was also showed (Kim et al 2010). Sequence variation in the PGC-1α gene modifies the age of onset of HD (Weydt et al 2009; Taherzadeh-Fard et al 2009). Stimulation of extrasynaptic NMDA receptors, which is detrimental, impairs the PGC-1α cascade in HD mice (Okamoto et al 2009). Impaired PGC-1α was shown to correlate with lipid accumulation in brown adipose tissue of HD transgenic mice (Phan et al 2009). These findings in concert, strongly implicate reduced expression of PGC-1α in HD pathogenesis. If impaired PGC-1α transcriptional activity is playing an important role in HD pathogenesis, then pharmacologic agents such as bezafibrate which increase its levels and activity might be beneficial.

With respect to tauopathies, although previous reports have shown that PPAR agonists can reduce amyloid-β (Aβ), studies to clarify the role of PPARs in Alzheimer's disease are necessary. In particular, the relationship between PPARs and the protein tau should be explored. Presently, whether a pan-PPAR agonist can be beneficial in models of Alzheimer's disease and tauopathy, specifically, the effect of bezafibrate administration in P301S mice was investigated Increased phosphorylation and accumulation of tau within neurons are important hallmarks of Alzheimer's disease and tauopathies. P301S transgenic mice, which carry the mutated human tau gene (P301S mutation), develop progressive tau pathology, behavioral (Scattoni et al 2010) and synaptic deficits (Yoshiyama et al 2007), and microglial activation (Yoshiyama et al 2007; Bellucci et al 2004).

There is a large body of evidence demonstrating the importance of PPARs in lipid metabolism, energy metabolism, and inflammation. Several groups have investigated the role of PPARs in the central nervous system and their effects in models of neurodegeneration (Heneka and Landreth 2007).

PPARγ agonists such as pioglitazones and rosiglitazones have been widely used in models of neurodegenerative diseases. Previously, it was reported that administration of pioglitazone extended survival, and attenuated neuronal loss, gliosis, and oxidative stress in a mouse model of amyotrophic lateral sclerosis (ALS) (Kiaei et al 2005). Similar results were found in the transgenic mouse models of Alzheimer's disease (AD) (Landreth 2007). These drugs had protective effects in transgenic mice modeling AD by reducing Aβ levels, inflammation, (Heneka et al 2005) and cerebrovascular dysfunction (Nicolakakis et al 2008). In addition to behavioral improvement (Escribano et al 2009), rosiglitazone also enhanced mitochondrial biogenesis (Strum et al 2007). Upregulation of PPARγ in neuroblastoma cells transfected with the human amyloid precursor gene (APP) was neuroprotective as evidenced by a reduction of $H_2O_2$-induced cell death and Aβ secretion (d'Abramo et al 2005). Other PPAR agonists have been tested as potential therapeutic agents for the treatment of neurodegenerative diseases. PPARα agonists, such as fenofibrate, show promising effects in mouse models of Parkinson's disease (PD) (Kreisler et al 2010) and brain injury (Besson et al 2005; Deplanque et al. 2003). In the latter, data showed that the neuroprotection was due to elevated antioxidant enzyme activities and reduced markers of inflammation. In primary neuronal cells, administration of Wy-14.463, a PPARα agonist, reduced Aβ-induced cell death, reactive oxygen species (ROS) production, and elevated calcium level by upregulating mitochondrial antioxidant enzymes (Santos et al 2005).

Tauopathies are a class of neurodegenerative diseases or effects of CNS trauma characterized by a pathological aggregation of tau protein in the human brain. The best known of these illnesses is Alzheimer's disease (AD), where tau protein is deposited within neurons in the form of neurofibrillary tangles (NFTs). Tangles are formed by hyperphosphorylation of a microtubule-associated protein known as tau, causing it to aggregate in an insoluble form (These aggregations of hyperphosphorylated tau protein are also referred to as PHF, or "paired helical filaments"). Other tauopathies include: Progressive supranuclear palsy; Dementia pugilistica (chronic traumatic encephalopathy); traumatic encephalopathy; Frontotemporal dementia and parkinsonism linked to chromosome 17; Lytico-Bodig disease (Parkinson-dementia complex of Guam); Tangle-predominant dementia; Ganglioglioma; gangliocytoma; Meningioangiomatosis; Subacute sclerosing panencephalitis; lead encephalopathy; tuberous sclerosis; Hallervorden-Spatz disease; lipofuscinosis; Pick's disease; corticobasal degeneration; Argyrophilic grain disease (AGD); corticobasal degeneration; Frontotemporal dementia; and Frontotemporal lobar degeneration. The non-Alzheimer's tauopathies are grouped together as members of "Pick's complex". For the purposes of this patent application, Parkinson's disease is not a tauopathy.

Although a number of studies have shown that agonists targeting individual PPARs have neuroprotective efficacy, there have not previously been studies of pan-PPAR agonists in transgenic mouse models of neurodegenerative diseases. Other approaches to achieving pan-PPAR effects include utilizing combinations of agonists that act either at the individual PPAR subtypes or at two PPAR subtypes. Examples of the latter include the glitazars, which operate as agonists of PPAR α and γ, and include aleglitazar, muraglitazar and tesaglitazar (Staels 2002). PPAR gamma agonists include the thiazolidinediones, also known as glitazones, which include rosiglitazone, pioglitazone, and troglitazone which are marketed drugs, as well as experimental agents MCC-555, rivoglitazone, and ciglitazone. NSAIDS such as ibuprofen and naproxen activate PPARγ (Dill et al 2010). Other PPARγ agonists include GW1929, azelacyl PAF, and BUT.13. PPAR alpha agonists include fibrates other than bezafibrate, such as CP-751461, CP868388, GW7647 and WY-14643. PPAR-beta/delta agonists include GW0742 and L165,041.

There is still a need to develop an effective potent therapeutic method for the treatment of neurodegenerative diseases, particularly for Huntington's disease and/or tauopathies, since there is as yet no cure for these disorders, and no therapy to delay the onset of symptoms.

SUMMARY OF THE INVENTION

The present invention provides a method of treating a neurodegenerative disease or disorder by administering to a subject in need a therapeutic composition comprising a pan-PPAR agonist, including wherein the pan PPAR agonist is bezofibrate. In certain embodiments, the neurodegenerative disease is Huntington's disease or a tauopathy. The invention provides that bezafibrate is beneficial in Huntington's Disease (HD) and in tauopathies. In HD, administration of bezafibrate provides significant improvements in behavior and survival, and prevents negative biochemical changes as well as neural and muscular degeneration. In tauopathy, treatment with bezafibrate reduces behavioral hyperactivity and disinhibition and reduces tau hyperphosphorylation, neurofibrillary tangle formation, inflammation, oxidative stress in spinal cord, and improved pathology in the brown adipose tissue.

The tauopathy may be a member of Pick's complex (aka Rick's disease and/or Rick's dementia), typically affects the frontal and/or anterolateral temporal lobes (also classified under the term frontotemporal dementia (FTD)). The member of Pick's complex/disease includes, but is not limited to, Progressive supranuclear palsy; Dementia pugilistica (chronic traumatic encephalopathy); traumatic encephalopathy; Frontotemporal dementia and parkinsonism linked to chromosome 17; Lytico-Bodig disease (Parkinson-dementia complex of Guam); Tangle-predominant dementia; Ganglioglioma; gangliocytoma; Meningioangiomatosis; Subacute sclerosing panencephalitis; lead encephalopathy; tuberous sclerosis; Hallervorden-Spatz disease; lipofuscinosis; Pick's disease; corticobasal degeneration; Argyrophilic grain disease (AGD); corticobasal degeneration; Frontotemporal dementia; or Frontotemporal lobar degeneration.

The present invention further provides a therapeutic composition, or a kit thereof, for treating a neurodegerative disease or disorder comprising an effective therapeutic amount of a Pan-PPAR agonist. In certain embodiments, the Pan-PPAR agonist is bezafibrate. In certain embodiments, the therapeutic composition further comprises a pharmaceutically suitable and acceptable carrier or adjuvant mixed with, and/or in conjuction with the Pan-PPAR agonist. The therapeutic composition of the present invention can be formulated in any pharmaceutically suitable and/or acceptable formulations for any suitable and/or acceptable administration routes, including, but not limited to, oral tablet or capsule, parental injectable solution or suspension, or subcutaneous patches. The therapeutic composition comprising a Pan-PPAR agonist can further be formulated to a suitable controlled-release, sustained-release, and/or delayed-release formulation. The therapeutic composition of the present invention can be administered alone, or in combination with any suitable agent or compound to enhance the therapeutic effect for the treatment of the neurodegenerative disease, and/or reduce any syndroms directed or indirected associtated with the disease and/or side effects resulted from the treatment.

The present invention further provides a method for treating a neurodegenerative disease utilizing a combination of agonists that together target all PPARs to achieve enhanced pan-PPAR neuroprotective effects, as evidenced in transgenic mouse models of human neurodegenerative diseases.

BRIEF DESCRIPTION OF THE DRAWINGS

Bezafibrate restores the PGC-1α signaling pathway in R6/2 mice.

Bezafibrate improves the behavioral phenotype and extends survival in R6/2 mice.

Figure 2A:
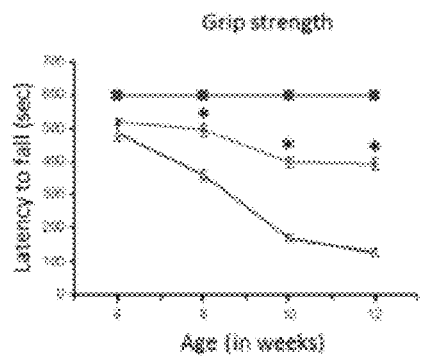

FIG. 2A illustrates a Grip strength analysis of R6/2 mice and their wild-type littermates on bezafibrate diet. There is a rapidly progressive reduction of muscle strength that is improved in bezafibrate treated R6/2 mice as compared to the R6/2 mice on a standard diet. *$p<0.001$, as compared to the R6/2 controls. (n=8 for each genotype, bezafibrate- or standard diet and bars represent S.E.M.).

Figure 2B:
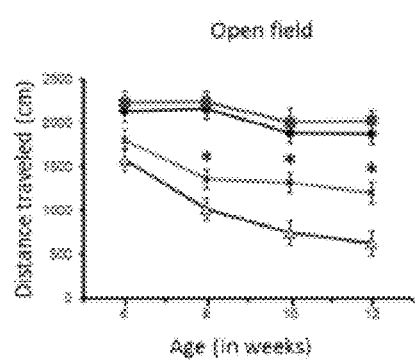

FIG. 2B illustrates a measurement of exploratory activity in R6/2 mice at different ages. R6/2 mice are significantly hypoactive as compared to their wild-type littermates (*$p<0.001$, n=8). Bezafibrate significantly restores normal activity and exploration.

Figure 2C:
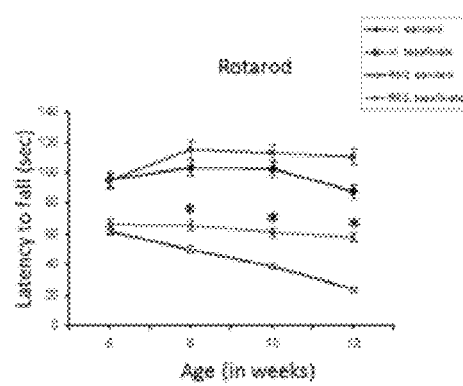

FIG. 2C illustrates an assessment of motor coordination in R6/2 mice on bezafibrate diet. R6/2 mice showed progressive, robust deficits on rotarod, with a significantly reduced latency to fall starting at 6 weeks. Bezafibrate treated mice remained on the rotarod longer than the untreated R6/2 mice.

Figure 2D:
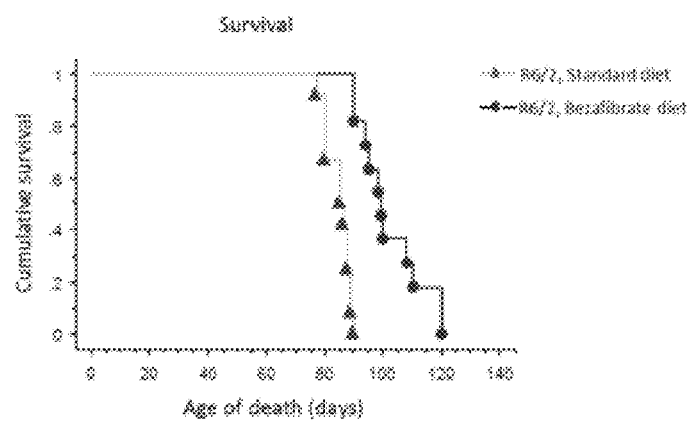

FIG. 2D illustrates a Kaplan-Meier survival plot of R6/2 mice on the bezafibrate diet in comparison to R6/2 mice on a standard diet. No mice in wild-type groups (bezafibrate or standard diet) died in the observed time frame. (n=10 in each group).

Bezafibrate prevents neurodegeneration and increases mitochondrial density.

FIG. 3A illustrates a Calbindin staining in the striatum of 12-week-old R6/2 mice and their wild-type littermates on bezafibrate or standard diet. FIG. 4 illustrates a stereological analysis of calbindin-immunoreactive medium spiny neuronal perikarya in the striatum. The decrease in neuron size is significantly ameliorated by bezafibrate treatment. *$p<0.05$.

FIG. 3B illustrates electron micrographs showing degenerated neurons in the striatum of R6/2 mice (quadrants a,b) and its amelioration by Bezafibrate (quandrants c,d). Quadrants a,b: Apoptotic neurons with condensed cytoplasm and abnormal nuclear shape showing margination and condensation of chromatin. The presence of large cytoplasmic vacuoles (bold arrow) and lysosome like dense bodies is also noted. Degenerated mitochondria (light arrow) and lot of empty spaces can also be seen. Quadrants c,d: In striata from bezafibrate treated R6/2 mice, the cytoplasm of the neuron is preserved and the axonal and dendritic profiles in the neuropil are relatively intact. Scale bars 2 μm. Magnification 10,000×.

Figure 3C:
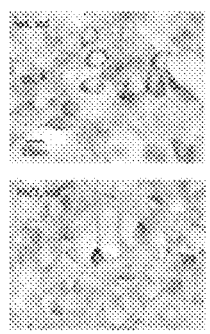
Figure 3C:
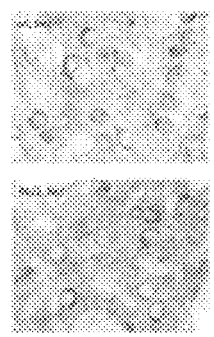
Figure 3C:
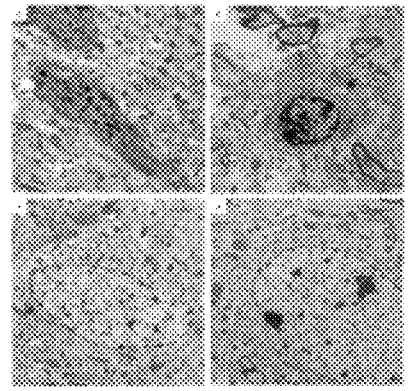
Figure 4:
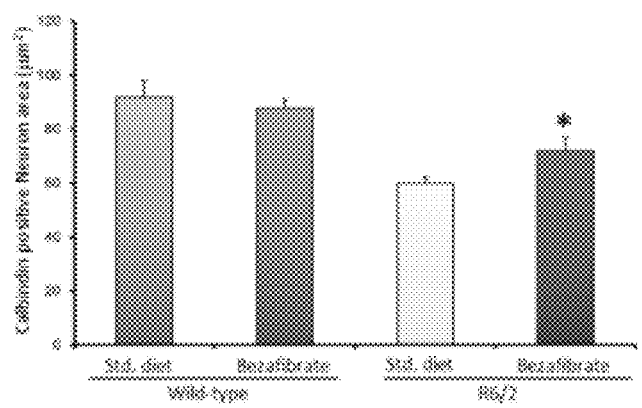

FIG. 3C illustrates a measurement of mitochondrial density in striatum region of the brain from R6/2 mice and their wild-type littermates on the bezafibrate diet or a standard diet. 10-15 neurons were counted per animal. n=3, *$p<0.05$ as compared to wild-type controls. §$p<0.05$ compared to R6/2 controls.

FIG. 4 illustrates a stereological analysis of calbindin-immunoreactive medium spiny neuronal perikarya in the striatum. The decrease in neuron size is significantly ameliorated by bezafibrate treatment. *$p<0.05$.

Figure 5:
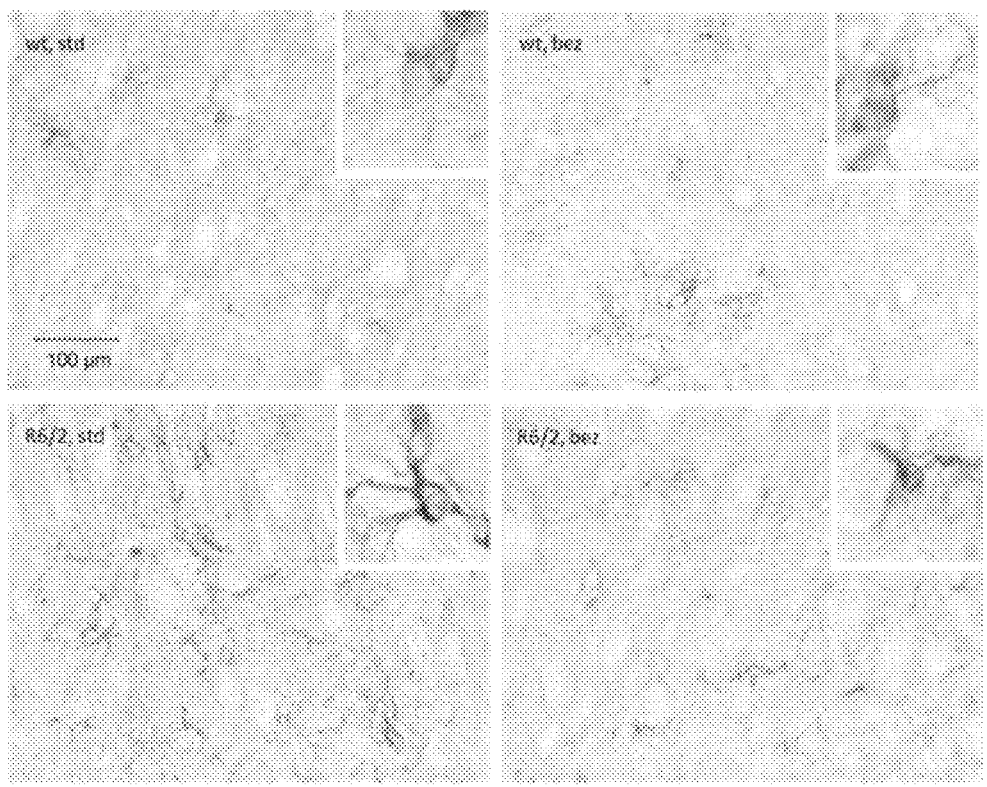

FIG. 5. Bezafibrate attenuates astrogliosis in R6/2 brains. Photomicrographs show glial fibrillary acidic protein (GFAP) immunoreactivity in the striatum of wild-type and R6/2 mice with or without bezafibrate treatment. GFAP-labeled hypertrophied astrocytes (inset) are evident in the striatum of R6/2 mice. Astrogliosis in the HD striatum is reduced by bezafibrate treatment.

Figure 6A:
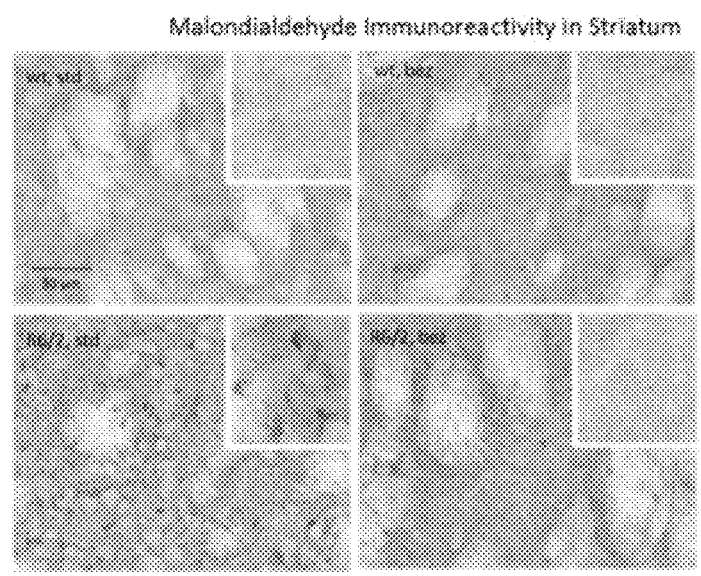
Figure 6B:
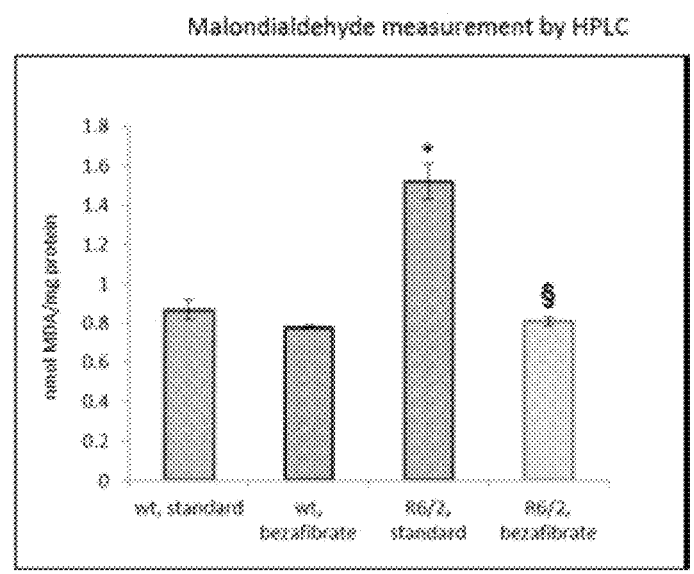

FIGS. 6A and 6B. Amelioration of oxidative stress in striatum of R6/2 mice by bezafibrate. FIG. 6A illustrates Malondialdehyde immunostaining in striatum of R6/2 mice and wild-type littermates on bezafibrate or standard diet. Insets show regions at a higher magnification. FIG. 6B illustrates a Bar-graph showing measurement of MDA levels by high-performance liquid chromatography (HPLC). *$p<0.001$ as compared to wild-type controls. §$p<0.001$ compared to R6/2 controls.

Figure 7A:
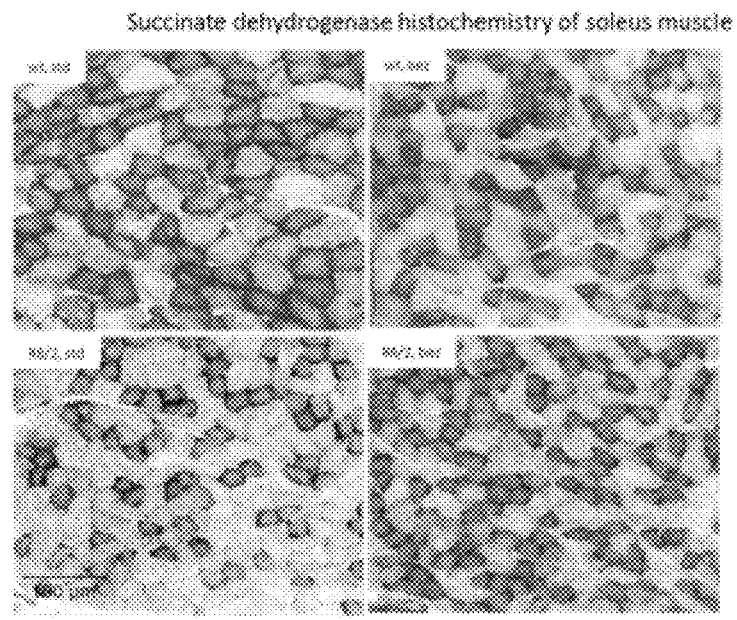
Figure 7B:
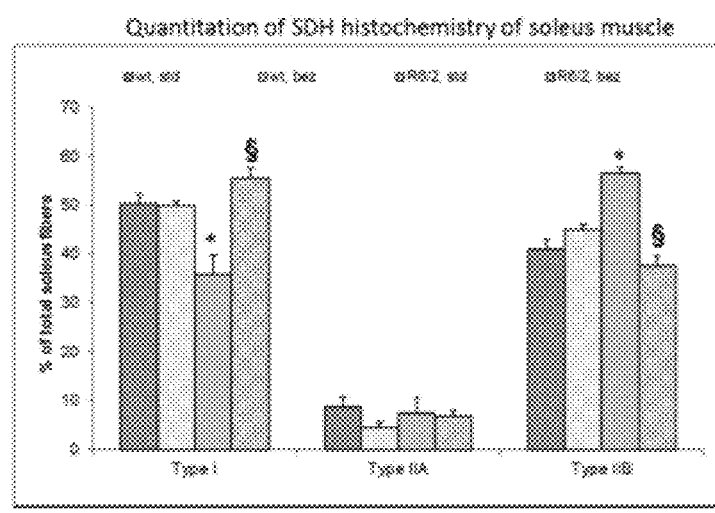
Figure 7C:
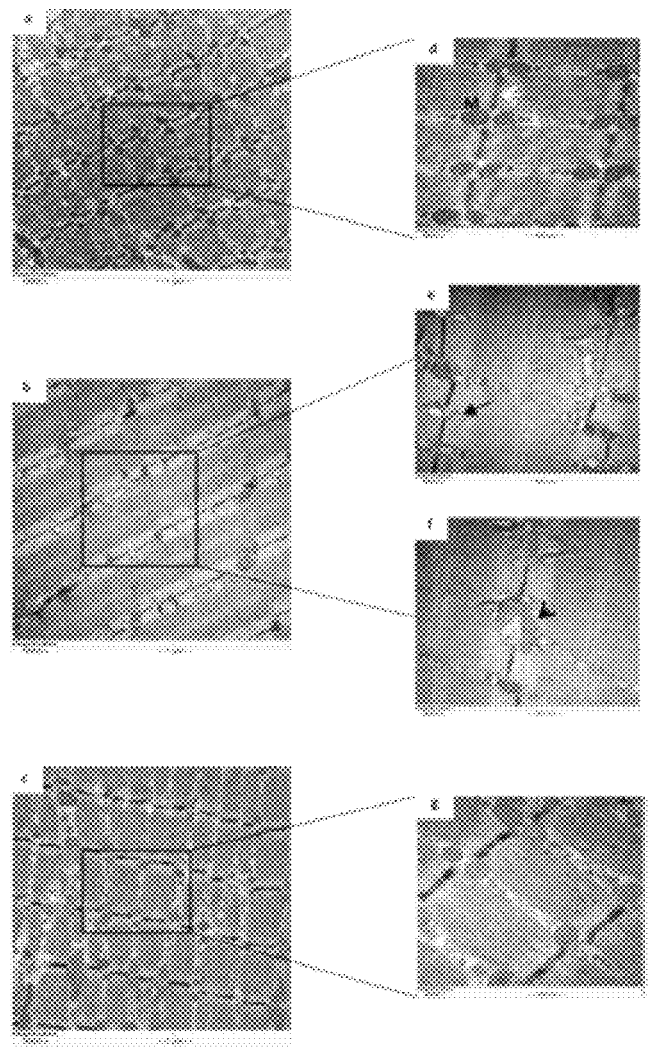

FIGS. 7A-7C. Fiber-type switching and abnormal ultrastructural abnormalities of muscle are reversed by bezafibrate. FIG. 7A illustrates histochemical staining for succinate dehydrogenase (SDH) in soleus muscle sections from wild-type and R6/2 mice with or without bezafibrate treatment. FIG. 7B shows quantitation of SDH histochemistry of soleus muscle. Decreased proportion of mitochondria enriched oxidative type I fibers can be seen in soleus from R6/2 mice as compared to wild-type. An enrichment of type I fibers and a decrease in glycolytic type IIB fibers can be seen in soleus muscle from R6/2 mice on bezafibrate diet. *$p<0.05$ as compared to wild-type controls. §$p<0.001$ compared to R6/2 controls. FIG. 7C illustrates a transmission electron microscopic analysis of soleus muscle from wild-type and R6/2 mice on standard or bezafibrate diet. Panel 'a' shows a micrograph from the soleus muscle of a wild-type mouse. Note the arrangement of mitochondria (M) along the Z-line (white arrow-head). The micrographs shown in panel a, b and c are at taken lower magnification (19,000×), and those in panels d, e, f and g are taken on higher magnification (48,000×). An altered morphology, number and alignment of mitochondria (black arrow) along the Z-lines can be seen in R6/2 mice under basal conditions. Structures resembling an autophagosome could also be noted (black arrow-head). Mitochondria are well organized and appear to be of normal shape and number in soleus muscle of R6/2 mice treated with bezafibrate (c, g).

Figure 8:
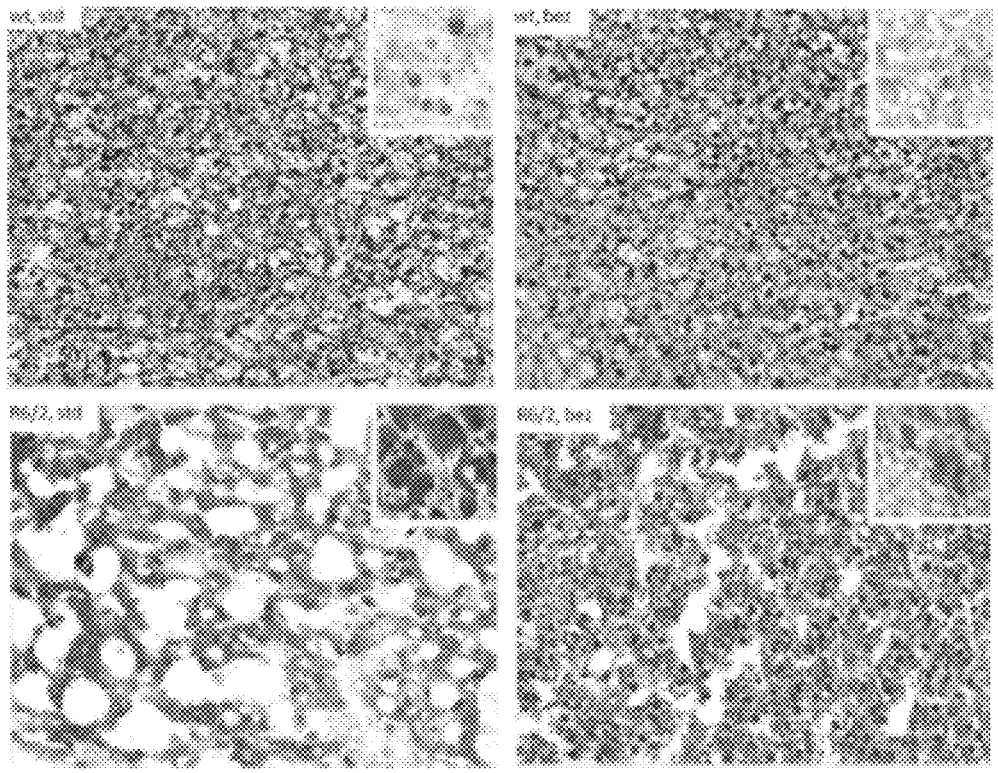

FIG. 8. Bezafibrate reduces BAT vacuolization in R6/2 mice. Brown adipose tissues of wild-type and R6/2 mice stained with hematoxylin-and-eosin showing increased vacuolization in the R6/2 mice. Oil red O staining (red staining, inset) revealed abundant accumulation of larger lipid droplets in the R6/2 mice as compared to wild-type mice. Bezafibrate reduces the accumulation of lipids and vacuolization in the R6/2 mice.

Figure 9:
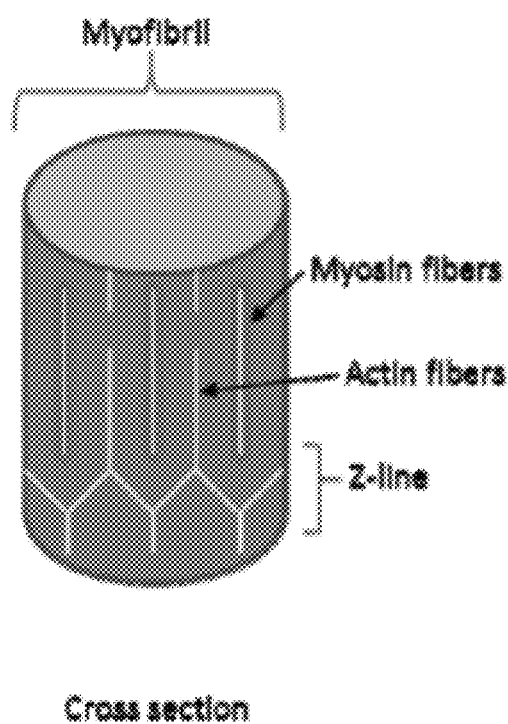

FIG. 9 shows the arrangement of myofibrils in muscle of a non-disease mouse.

Figure 10:
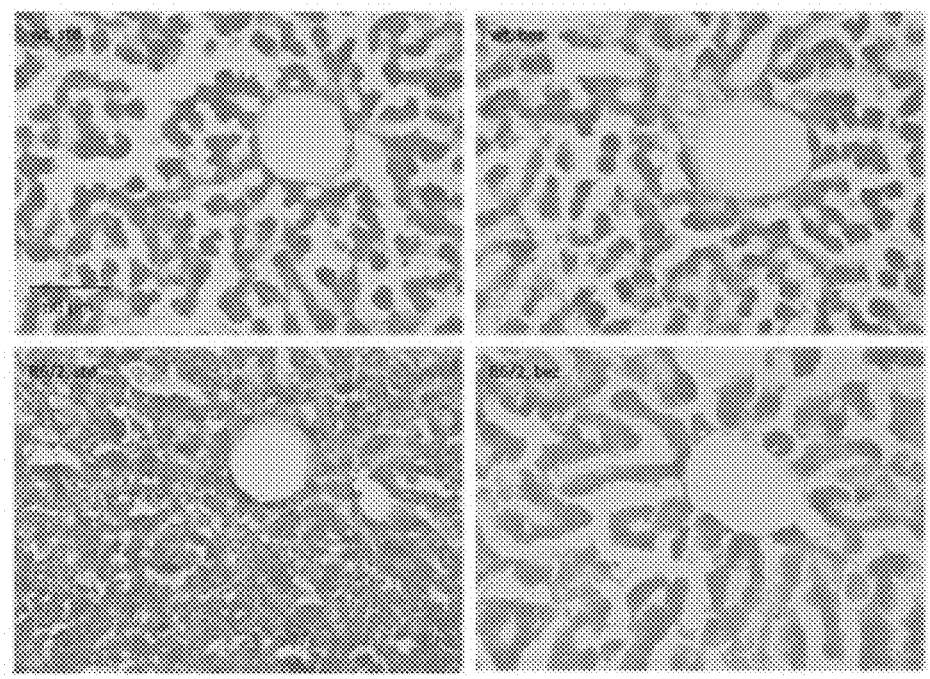

FIG. 10 reports the effect of bezafibrate treatment in liver of R6/2 mice and their wild-type littermates. H&E staining of the liver of wild-type and R6/2 mice with or without bezafibrate treatment. Vaculolization of hepatocytes is present in the liver of R6/2 mice at baseline. Liver morphology appears normal in R6/2 mice treated with bezafibrate.

Figure 11A:
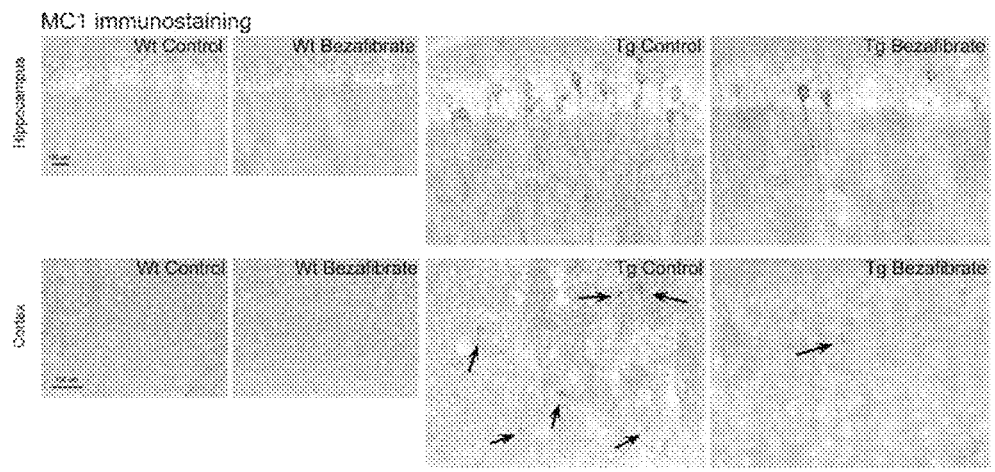
Figure 11B:
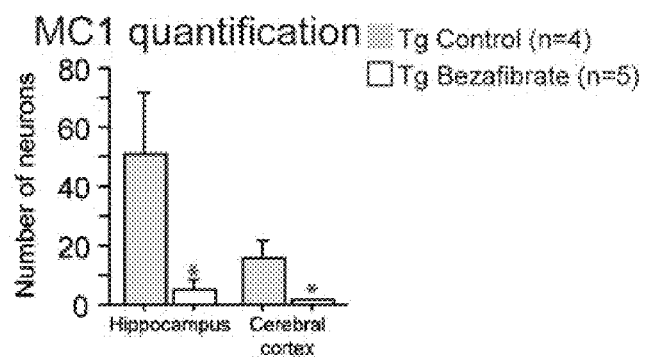
Figure 12A:
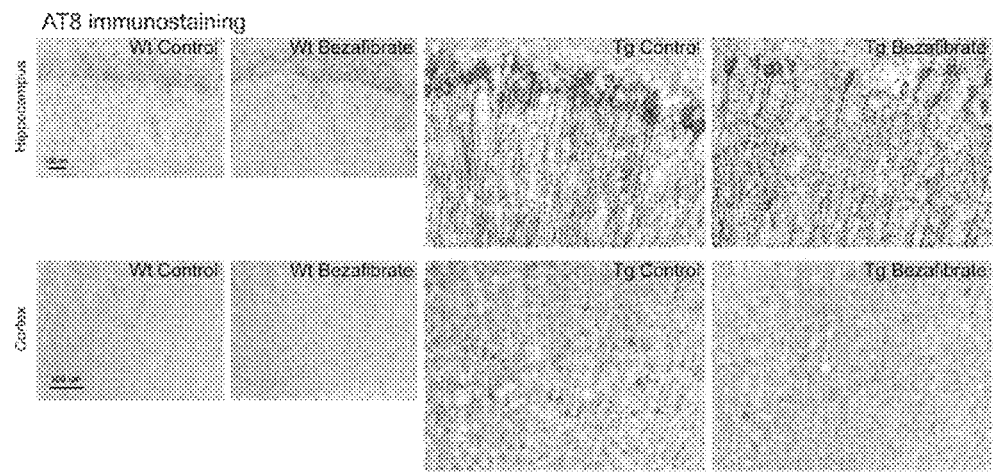
Figure 12B:
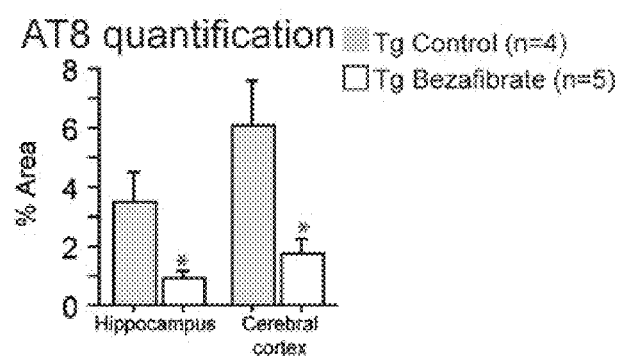

FIGS. 11A, 11B, 12A, and 12B. Bezafibrate treatment reduced tau pathology in P301S mice. MC1 antibodies in the cortex and hippocampus are shown in FIG. 11A (scale bar: 100 μm). The number of MC1 positive neurons in the hippocampus and cortex in P301S mice fed control diet (Tg Control) and P301S mice fed bezafibrate diet (Tg Bezafibrate) is shown in FIG. 11B. Immunohistochemical staining with AT8 is shown in FIGS. 12A and 12B Percent area covered by AT8 immunoreactivity for the hippocampus and cortex is shown in FIG. 12B. Administration of bezafibrate in P301S mice reduced tau phosphorylation and tangle formation (Fisher PLSD, *p<0.05, n=4-7).

Figure 13A:
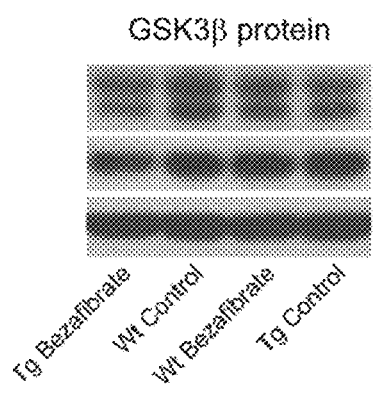
Figure 13B:
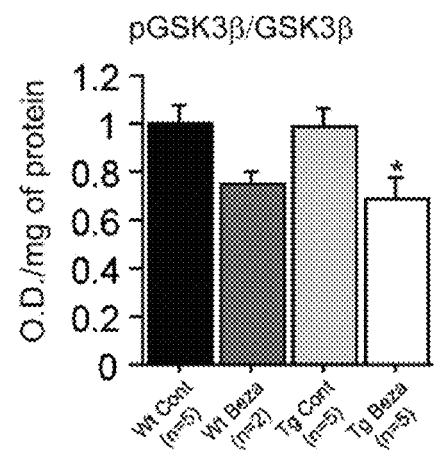

FIGS. 13A and 13B. Bezafibrate decreased phospho-GSK3β expression. Western blots of cortical phospho-GSK3β, total GSK3β (FIG. 13A), and quantification by optical densities (FIG. 13B) in P301S mice fed control diet (Tg Cont) and P301S mice fed bezafibrate diet (Tg Beza). Bezafibrate treatment reduced phospho-GSK3l3 level in P301S mice (Fisher PLSD, *p<0.05, n=4-6).

Figure 14:
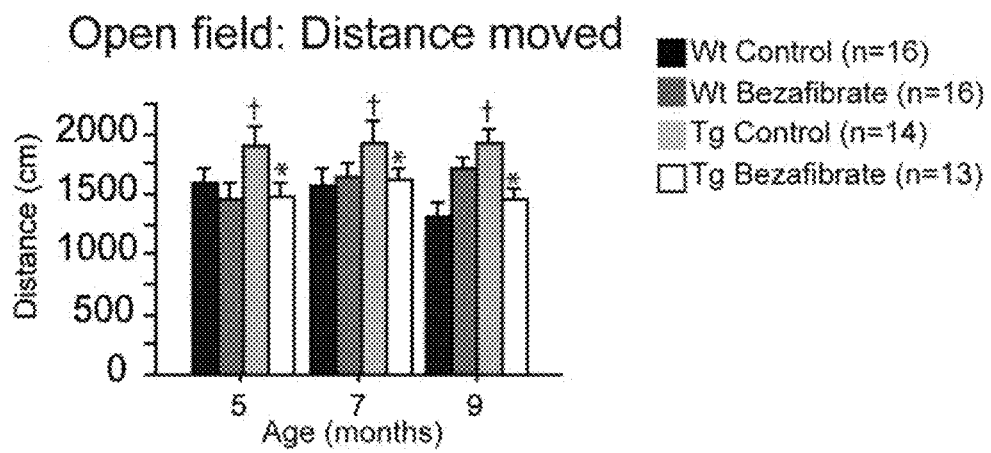
Figure 15:
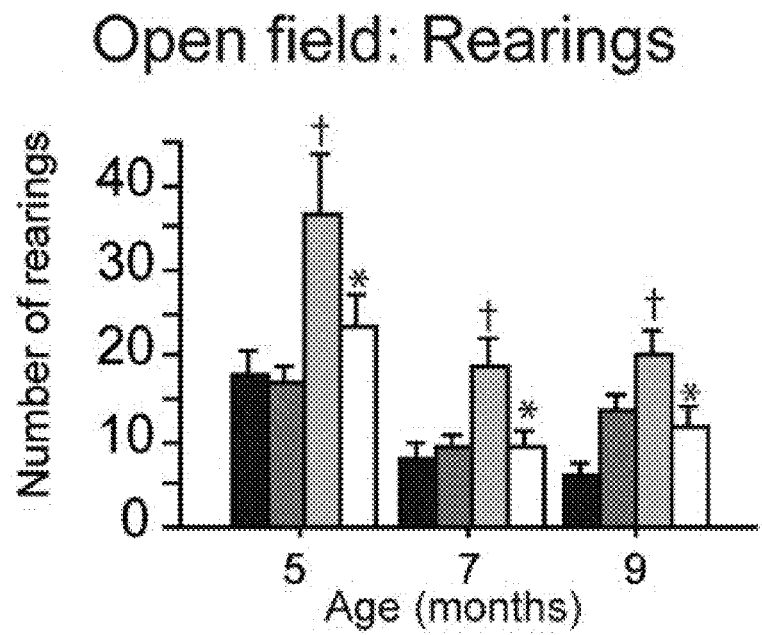
Figure 16:
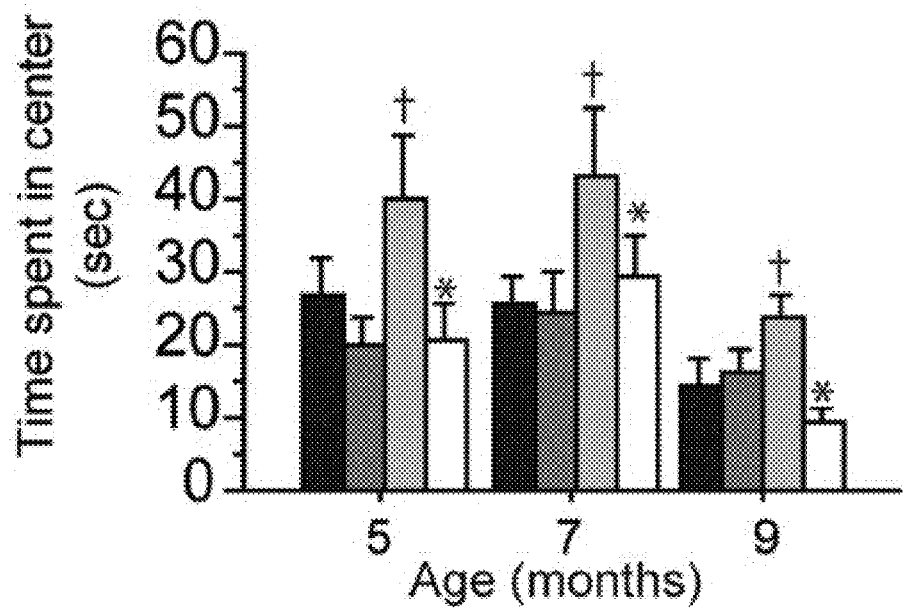

FIGS. 14-16. Bezafibrate treatment rescued behavioral abnormalities in P301S mice. Distance moved (FIG. 14), rearings (FIG. 15), and anxiety (time spent in the center) (FIG. 16) of the openfield in wild-type mice fed control diet (Wt Control), wild-type mice fed bezafibrate diet (Wt Bezafibrate), P301S mice fed control diet (Tg Control), and P301S mice fed bezafibrate diet (Tg Bezafibrate). P301S mice were hyperactive and disinhibited in the openfield as compared to wild-type littermates (Fisher PLSD, † p<0.05, n=16). Bezafibrate treatment rescued behavioral abnormalities in P301S mice (Fisher PLSD, *p<0.05, n=15-16).

Bezafibrate had anti-inflammatory effects in P301S mouse brains. Administration of bezafibrate reduced microglial activation in the hippocampus of P301S mice (Fisher PLSD, * p<0.05, n=5-6). In P301S mice, bezafibrate treatment decreased COX2 expression (Fisher PLSD, * p<0.05, n=5-6).

Bezafibrate reduced oxidative stress in the spinal cord of P301S mice. Administration of bezafibrate reduced MDA level and immunoreactivity in P301S mice (Fisher PLSD, *p<0.05, n=4-6). P301S mice had increased nitrotyrosine level relative to their wild-type littermates (Fisher PLSD, † p<0.05, n=3-5). Administration of bezafibrate reduced nitrotyrosine level in the spinal cord of P301S mice (Fisher PLSD, *p<0.05, n=5-6).

Bezafibrate reduced oxidative stress in the spinal cord by activating the PGC1α pathway. P301S mice fed bezafibrate diet had increased PGC1α level as compared to P301S mice fed control diet (n=6). Bezafibrate treated P301S mice had elevated NRF1 levels as compared to control P301S mice (Fisher PLSD, *p<0.05, n=5-6).

Bezafibrate improved brown adipose pathology by activating the PGC1α pathway. P301S mice had increased vacuolation as compared to wild-type littermates, which was rescued by bezafibrate treatment (n=4-5). P301S mice had decreased expression of PGC1α compared to wild-type littermates. Bezafibrate elevated gene expression of PGC1α related genes in P301S mice (n=4-5). Immunohistochemical staining of PGC1α (C) in brown fat of wild-type mice fed control diet (Wt Control), wild-type mice fed bezafibrate diet (Wt Bezafibrate), P301S mice fed control diet (Tg Control), and P301S mice fed bezafibrate diet (Tg Bezafibrate) (scale bar: 100 μm). PGC1α was localized at the periphery of enlarged lipid droplets in P301S mice. After bezafibrate treatment, PGC1α was diffuse in the cytoplasm as observed in the wild-type littermates (n=4-5). In P301S mice, PGC1α levels were decreased which may have lead to a reduction of mitochondrial biogenesis, causing an enlargement of lipid droplets. Bezafibrate treatment rescued PGC1α level which may have lead to an increase of mitochondrial biogenesis, preventing vacuolation.

Bezafibrate reduced body weight in mice. Male (FIG. 17A) and female (FIG. 17B) body weights in wild-type mice fed control diet (Wt Control), wild-type mice fed bezafibrate diet (Wt Bezafibrate), P301S mice fed control diet (Tg Control), and P301S mice fed bezafibrate diet (Tg Bezafibrate). Bezafibrate treated P301S and wild-type mice had decreased body weights relative to control treated animals (Fisher PLSD, *p<0.05, n=15-16). Bezafibrate treated P301S and wild-type mice had increased latency to fall relative to control treated animals (Fisher PLSD, *p<0.05, n=15-16).

Bezafibrate did not alter total tau level in P301S mice. Administration of bezafibrate in P301S mice did not significantly reduce tau hyperphosphorylation (Fisher PLSD, *p>0.05, n=5). There was no difference in the levels of total tau after bezafibrate treatment in P301S mice (Fisher PLSD, p>0.05, n=6-7).

Bezafibrate reduced GFAP immunoreactivity in the hippocampus.

Bezafibrate did not affect mitochondrial enzymes in P301S brains.

Figure 18A:
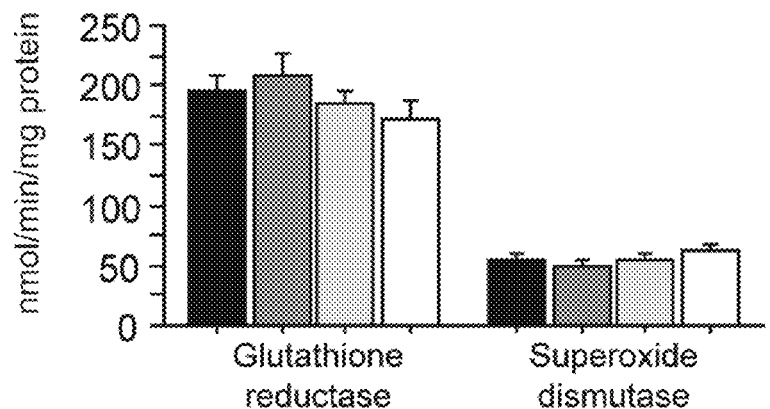
Figure 18B:
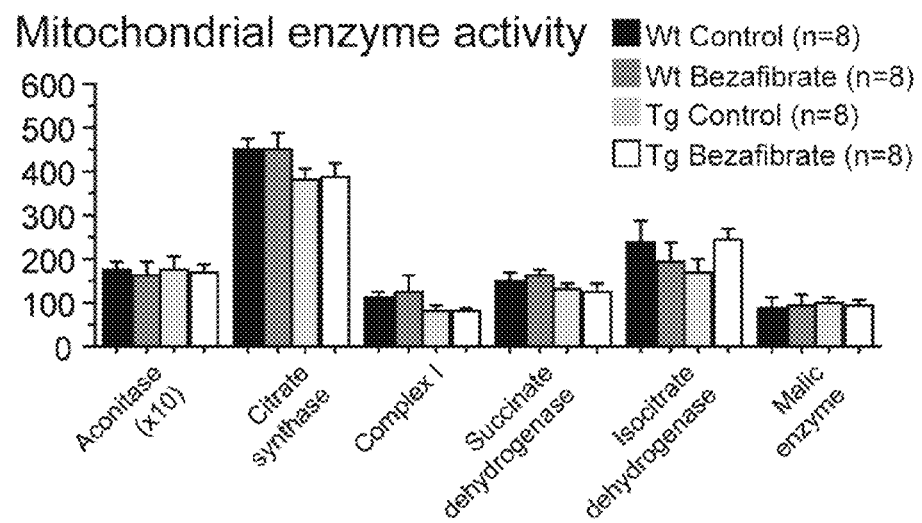

FIGS. 18A and 18B illustrate enzymatic activity of glutathione reductase, isocitrate dehydrogenase, malic enzyme and superoxide dismutase in brains of wild-type mice fed control diet (Wt Control), wild-type mice fed bezafibrate diet (Wt Bezafibrate), P301S mice fed control diet (Tg Control), and P301S mice fed bezafibrate diet (Tg Bezafibrate). No differences were observed in enzymes of the electron transport chain after bezafibrate treatment in P301S mice. Wild-type mice fed bezafibrate had elevated complex I level compared to all other groups (n=8).

DETAILED DESCRIPTION OF THE INVENTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The present invention provides a method for therapeutic treatment of a neurodegenerative disease using a Pan-PPAR agonist. In certain embodiments, the Pan-PPAR agonist is bezafibrate. In light of the data obtained from the well known and conventional acceptable mouse model of Huntington's disease, such as R6/2 mice, the present invention provides that bezafibrate improves behavioral phenotype, increased survival, and the induction of the PGC-1α signaling pathway, as well as reduces neuropathological features and significant increases mitochondrial density in striatum of R6/2 mice treated with bezafibrate, suggesting that bezafibrate can be proved to be an effective neuroprotective agent for treatment of HD.

Tauopathies are a class of neurodegenerative diseases or effects of CNS trauma characterized by a pathological aggregation of tau protein in the human brain. The best known of these illnesses is Alzheimer's disease (AD). The present invention provides that the protective effects of the pan-PPAR agonist bezafibrate in P301S mice, the well known and conventional acceptable tauopathy mouse model in the art, were present at various levels. In the brain, bezafibrate induced tau degradation and prevented tau phosphorylation. By downregulating microglia and COX2, bezafibrate also reduced inflammation. In the spinal cord and the brown adipose tissue, bezafibrate acted by inducing the PGC1α pathway and mitochondrial biogenesis, which reduced oxidative stress and brown fat vacuolation. Data from initial clinical trials using specific PPAR agonists in AD were encouraging. The present invention for the first provides in vivo evidence that PPAR activation exerts beneficial effects and ameliorates the behavioral and neuropathologic effects of tauopathy. Thus, the use of potent pan-PPAR agonists may lead to improve efficacy in the treatment of neurodegenerative diseases.

The present invention thus demonstrates that a pan-PPAR agonist, such as bezafibrate, provides neuroprotection in transgenic mouse models of both tauopathy and Huntington's disease. These transgenic mice have genetic mutations which cause human illness. Bezafibrate exerts neuroprotective effects in these models. These beneficial effects are improved over those previously reported using selective PPAR agonists, such as thiazolidinediones.

As used herein, the term "Pan-PPAR agonist" refers to any molecule that is capable to activate PPAR receptor and/or one or more PPAR receptor subtypes, now known or later discovered, and/or the PPAR-RXR heterodimer, thus, increasing a biological activity regulated through the PPAR receptor and its downsteam signal transduction pathways. Molecules that can act as Pan-PPAR agonist include endogeneous and/or snythestic PPAR ligands, including, but not limited to, Abs or Ab fragments, fragments or variants of endogenous PPAR receptors, peptides, antisense oligonucleotides, small organic molecules, etc. The present invention encompasses any PPAR agonists, now known or later discovered, including, but not limited to, PPARα agonists: bezafibrate and other fibrates, such as CP-751461, CP868388, GW7647 and WY-14643; PPARγ agonists: the thiazolidinediones (aka glitazones), such as, rosiglitazone, pioglitazone, troglitazone, MCC-555, rivoglitazone, ciglitazone, GW1929, azelacyl PAF, BUT.13, and NSAIDS, such as ibuprofen, fenoprofen, indomethacin, and naproxen; PPARα/γ agonists: glitazars, such as aleglitazar, muraglitazar and tesaglitazar; and PPARβ/δ agonists: GW0742, W501516, and L165,041.

The identified Pan-PPAR agonists treat, inhibit, control and/or prevent, or at least partially arrest or partially prevent, neurodegenerative disorders and/or diseases, such as Huntington's Disease (HD) and/or tauopathies, such as Alzheimer's disease (AD), and can be administered to a subject at therapeutically effective doses for the inhibition, prevention, prophylaxis or therapy. The Pan-PPAR agonists of the present invention comprise a therapeutically effective dosage of a Pan-PPAR agonist, a term which includes therapeutically, inhibitory, preventive and prophylactically effective doses of the Pan-PPAR agonist of the present invention and is more particularly defined above. Without being bound to any particular theory, applicants surmise that these pharmaceutical Pan-PPAR agonists are effective in treatment when administered to a subject suffering from a neurodegenerative disease or disorder. The subject is preferably an animal, including, but not limited to, mammals, reptiles and avians, more preferably horses, cows, dogs, cats, sheep, pigs, and chickens, and most preferably human.

The data obtained from the animal model studies can be used in formulating a range of dosages for use in humans and other mammals. The dosage of such a Pan-PPAR agonist lies preferably within a range of circulating plasma or other bodily fluid concentrations that include the $ED_{50}$ with little or no toxicity. The dosage may vary within this range depending upon the dosage form employed and the route of administration utilized. For any Pan-PPAR agonist of the invention, the therapeutically effective dose can be estimated initially from animal studies. A dosage may be formulated in animal models to achieve a circulating plasma concentration range that includes the $IC_{50}$ (the concentration of the test Pan-PPAR agonist that achieves a half-maximal inhibition of symptoms) as determined in cell culture. Such information can be used to more accurately determine useful dosages in humans and other mammals. Levels of a Pan-PPAR agonist in plasma may be measured, for example, by high performance liquid chromatography.

The amount of a Pan-PPAR agonist that may be combined with a pharmaceutically acceptable carrier to produce a single dosage form will vary depending upon the host treated and the particular mode of administration. It will be appreciated by those skilled in the art that the unit content of a Pan-PPAR agonist contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a neurodegenerative disease or condition with the Pan-PPAR agonist of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a Pan-PPAR agonist delivery system is utilized and whether the Pan-PPAR agonist is administered as a pro-drug or part of a drug combination. Thus, the dosage regime actually employed may vary widely from subject to subject.

The Pan-PPAR agonist, such as bezafibrate, of the present invention may be formulated by known methods for administration to a subject using several routes which include, but are not limited to, parenteral, oral, topical, intradermal, intramuscular, intraperitoneal, intravenous, subcutaneous, intranasal, epidural, intercranial, and ophthalmic routes. The individual Pan-PPAR agonist may also be administered in combination with one or more other Pan-PPAR agonist of the present invention and/or together with other biologically active or biologically inert agents. Such biologically active or inert agents may be in fluid or mechanical communication with the Pan-PPAR agonist(s) or attached to the Pan-PPAR agonist(s) by ionic, covalent, Van der Waals, hydrophobic, hydrophillic or other physical forces. It is preferred that administration is localized in a subject, but administration may also be systemic.

The Pan-PPAR agonist including bezafibrate of the present invention may be formulated by any conventional manner using one or more pharmaceutically acceptable carriers and/or excipients. Thus, the Pan-PPAR agonists and their pharmaceutically acceptable salts and solvates may be specifically formulated for administration, e.g., by inhalation or insufflation (either through the mouth or the nose) or oral, buccal, parenteral or rectal administration. The Pan-PPAR agonists may take the form of charged, neutral and/or other pharmaceutically acceptable salt forms. Examples of pharmaceutically acceptable carriers include, but are not limited to, those described in REMINGTON'S PHARMACEUTI- CAL SCIENCES (A. R. Gennaro, Ed.), 20th edition, Williams & Wilkins P A, USA (2000).

The Pan-PPAR agonists may also take the form of solutions, suspensions, emulsions, tablets, pills, capsules, powders, controlled- or sustained-release formulations and the like. Such formulations will contain a therapeutically effective amount of the Pan-PPAR agonist, preferably in purified form, together with a suitable amount of carrier so as to provide the form for proper administration to the patient. The formulation should suit the mode of administration.

The Pan-PPAR agonists may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the Pan-PPAR agonist may be formulated in powder form for constitution with a suitable vehicle, such as sterile pyrogen-free water, before use. For example, a Pan-PPAR agonist, such as bezafibrate, suitable for parenteral administration may comprise a sterile isotonic saline solution containing between 0.1 percent and 90 percent weight per volume of the compound. By way of example, a solution may contain from about 0.1 percent to about 20 percent, more preferably from about 0.55 percent to about 17 percent, more preferably from about 0.8 to about 14 percent, and still more preferably about 10 percent of the Pan-PPAR agonist, such as bezafibrate. The solution or powder preparation may also include a solubilizing agent and a local anesthetic such as lignocaine to ease pain at the site of the injection. Other methods of parenteral delivery of Pan-PPAR agonists will be known to the skilled artisan and are within the scope of the invention.

For oral administration, the Pan-PPAR agonist, such as bezafibrate, may take the form of tablets or capsules prepared by conventional means with pharmaceutically acceptable excipients such as binding agents, fillers, lubricants and disintegrants. The tablets or capsules may optionally be coated by methods well known in the art. If binders and/or fillers are used with the Pan-PPAR agonist of the invention, they are typically formulated as about 50 to about 99 weight percent of the Pan-PPAR agonist. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound. In addition, the compounds of the present invention may be formulated for buccal administration in the form of tablets or lozenges formulated in a conventional manner. Other methods of oral delivery of compounds will be known to the skilled artisan and are within the scope of the invention.

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a Pan-PPAR agonist, such as bezafibrate, that produces the desired therapeutic effect, and gradually and continually release other amounts of the Pan-PPAR agonist to maintain the level of therapeutic effect over an extended period of time. In order to maintain a near-constant level of a Pan-PPAR agonist in the body, the Pan-PPAR agonist can be released from the dosage form at a rate that will replace the amount of Pan-PPAR agonist being metabolized and/or excreted from the body. The controlled-release of a Pan-PPAR agonist, such as bezafibrate, may be stimulated by various inducers, e.g., change in pH, change in temperature, enzymes, water, or other physiological conditions or molecules.

Controlled-release systems may include, for example, an infusion pump which may be used to administer the Pan-PPAR agonist(s) in a manner well known and accepted to those of ordinary skill in the art. Typically, using such a system, the Pan-PPAR agonist(s) is administered in combination with a biodegradable, biocompatible polymeric implant that releases the Pan-PPAR agonist, such as bezafibrate, over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The Pan-PPAR agonists of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of Pan-PPAR agonists will be known to the skilled artisan and are within the scope of the invention.

Sustained-release preparations may also be prepared, such as semi-permeable matrices of solid hydrophobic polymers containing the Pan-PPAR agonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as injectable microspheres composed of lactic acid-glycolic acid copolymer, and poly-D-(−)-3-hydroxybutyric acid. While polymers such as ethylene-vinyl acetate and lactic acid-glycolic acid enable release of molecules for over 100 days, certain hydrogels release proteins for shorter time periods and may be preferred.

The Pan-PPAR agonist of the present invention can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions. The formulations to be used for in vivo administration are highly preferred to be sterile. This is readily accomplished by filtration through sterile filtration membranes or any of a number of techniques.

The Pan-PPAR agonist, such as bezafibrate or others, may also be formulated as a depot preparation. Such long-acting formulations may be administered by implantation (e.g., subcutaneously or intramuscularly or intercranially) or by injection. Accordingly, the Pan-PPAR agonists may be formulated with suitable polymeric or hydrophobic materials such as an emulsion in an acceptable oil or ion exchange resins, or as sparingly soluble derivatives such as a sparingly soluble salt. Other methods of depot delivery of the Pan-PPAR agonists will be known to the skilled artisan and are within the scope of the invention.

Various other delivery systems are known in the art and can be used to administer the Pan-PPAR agonists of the invention. Moreover, these and other delivery systems may be combined and/or modified to optimize the administration of the Pan-PPAR agonists of the present invention.

A therapeutcally effective amount of a Pan-PPAR agonist relates generally to the amount needed to achieve a therapeutic objective, administration rate, and depletion or metabolic rate of the Pan-PPAR agonist from a subject. Common ranges for therapeutically effective doses may be, as a nonlimiting example, from about 0.1 mg/kg body weight to about 50 mg/kg body weight. Dosing frequencies may range, for example, from twice daily to once a week.

The Pan-PPAR agonists can be synthesized chemically and/or produced by any suitable methology and/or technology known to those skilled in the art. Formulations may also contain more than one active Pan-PPAR agonists for a particular treatment, preferably those with activities that do not adversely affect each other. The composition may comprise an agent that enhances function, as a nonlimiting example, other types of neuroprotective agents, a cytotoxic agent, cytokine, chemotherapeutic agent or growth-inhibitory agent.

In various embodiments, the present invention can also involve kits. Such kits can include the Pan-PPAR agonists of the present invention and, in certain embodiments, instructions for administration. When supplied as a kit, different components of a Pan-PPAR agonist formulation can be packaged in separate containers and admixed immediately before use. Such packaging of the components separately can, if desired, be presented in a pack or dispenser device which may contain one or more unit dosage forms containing the Pan-PPAR agonists. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may also include reagents in separate containers such as, for example, sterile water or saline to be added to the active component packaged separately. For example, sealed glass ampules may contain purified Pan-PPAR agonist and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit, or supplied as electronic mail.

The present invention provides a method for treating a neurodegenerative disease or disorder using one or more Pan-PPAR agonist. In certain embodiments, the neurodegenerative disease is Huntington's disease and/or tauopathies, including, but not limited to, Alzheimer's disease (AD), Pick's complex or Pick' disease or dementia, such as Progressive supranuclear palsy; Dementia pugilistica (chronic traumatic encephalopathy); traumatic encephalopathy; Frontotemporal dementia and parkinsonism linked to chromosome 17; Lytico-Bodig disease (Parkinson-dementia complex of Guam); Tangle-predominant dementia; Ganglioglioma; gangliocytoma; Meningioangiomatosis; Subacute sclero sing panencephalitis; lead encephalopathy; tuberous sclerosis; Hallervorden-Spatz disease; lipofuscinosis; corticobasal degeneration; Argyrophilic grain disease (AGD); corticobasal degeneration; Frontotemporal dementia; or Frontotemporal lobar degeneration.

EXAMPLES

The present description is further illustrated by the following examples, which should not be construed as limiting in any way. The contents of all cited references (including literature references, issued patents, published patent applications as cited throughout this application) are hereby expressly incorporated by reference.

Example 1

Bezafibrate's Effects on the Huntington Disease (Hd) Materials and Methods for Hd Work Reagents Bezafibrate, malondialdehyde standard (MDA, 98% purity) and other chemicals were purchased from Sigma (St. Louis, Mo., USA). R6/2 mice were from Jackson Laboratory, Bar Harbor, USA. Anti-calbindin was from Chemicon, Temecula, Calif., USA; anti-malondialdehyde modified protein was a gift from Dr. Craig Thomas and anti-glial fibrillary acidic protein was from Dako, Denmark. The sequences of all the primers used in this study have been published elsewhere and/or are available on request (Chaturvedi et al. 2009; Chaturvedi et al 2010).

Animal Treatment

All experiments were conducted within National Institutes of Health guidelines for animal research and were approved by the Weill Cornell Medical College Animal Care and Use Committee. The animals were kept on a 12-hr light/dark cycle, with food and water available ad libitum. Mice were fed standard diet containing 0.5% bezafibrate or standard diet (Purina-Mills Richmond, Ind., USA), starting right after weaning up to 3 months of age.

Real-Time PCR

Total RNA was isolated from liquid nitrogen snap frozen tissues using Trizol reagent, according to manufacturer's instructions (Invitrogen, Carlsbad, Calif., USA). Genomic DNA was removed using RNase free DNase (Ambion) in RNA pellets re-suspended in DEPC-treated water (Ambion). Total RNA purity and integrity was confirmed by ND-1000 NanoDrop (NanoDrop Technologies). Equal amounts of RNA were reverse transcribed using the cDNA Synthesis Kit (Invitrogen, USA). Real-time RT-PCR was performed using the ABI prism 7900 HT sequence detection system (Applied Biosystems, Foster City, Calif.). Expression of the gene β-actin served as a control to normalize values. Relative expression was calculated using the ΔΔCt method.

Behavioral Tests

Experimenters were blind to the genotype during all testing, at least until the appearance of a robust behavioral phenotype in the mutants. We utilized a behavioral testing battery consisting of: rotarod, grip strength and open field. On the rotarod (Economex, Columbus Instruments, Columbus, Ohio, USA), mice were tested over 3 consecutive days, in three 5 min-trials, with an accelerating speed (from 0 to 40 RPM in 5 min) separated by a 30-min inter-trial interval. The latency to fall from the rod was recorded. Exploratory behavior was recorded in the open-field (45 cm×45 cm; height: 20 cm), for 10 min per day using a video tracking system (Ethovision 3.0, Noldus Technology, Attleborough, Mass., USA) and averaged over 3 days. For the grip strength test, mice were held by the tail and placed on a wire-grill apparatus so that they grabbed the handle with both front paws and then gently pulled back until they released it. Each session consisted of 5 trials.

Immunohistochemistry

Mice intended for neuropathologic analysis were deeply anesthetized by intraperitoneal injection of sodium pentobarbital and perfused with 0.9% sodium chloride followed by 4% paraformaldehyde. Post-fixation, staining and processing of brain, muscle, BAT and liver samples were performed as described previously (Chaturvedi et al. 2009; Chaturvedi et al 2010; Stack et al 2010).

Transmission Electron Microscopy

Transmission electron microscopy was performed using previously published methods (13), except that for striatum the post-fixation was performed in 1% OsO4- in 0.1M buffer instead of 1% OsO4-1.5% K-ferricyanide (soleus) for 60 min at room temperature.

High-Performance Liquid Chromatography

The HPLC determination of MDA was carried out by a method modified from a previous report (Agarwal and Chase 2002). The HPLC system consisted of a Waters 717plus autosampler, 515 isocratic pump and 470 scanning fluorescence detector (Waters, Milford, Mass.). Pump flow-rate was 1.0 ml/min with mobile phase comprised of acetonitrile-buffer (40:60, v/v). The buffer was 50 mM potassium monobasic phosphate (anhydrous) with an adjusted pH of 6.8 using 5 M potassium hydroxide. The fluorescence detector was set at an excitation wavelength of 515 nm and emission wavelength of 553 nm. The column was an ESA 150×3 mm C18 column with particle size 3 μm (ESA, Inc Chelmsford, Mass.) placed in a column warmer set to 30° C. Peak heights were integrated by an ESA 501 chromatography data system (ESA, Inc Chelmsford, Mass.).

Results of HD Work

Bezafibrate Induces a Battery of Genes in the PGC-1α Signaling Pathway

Figure 1A:
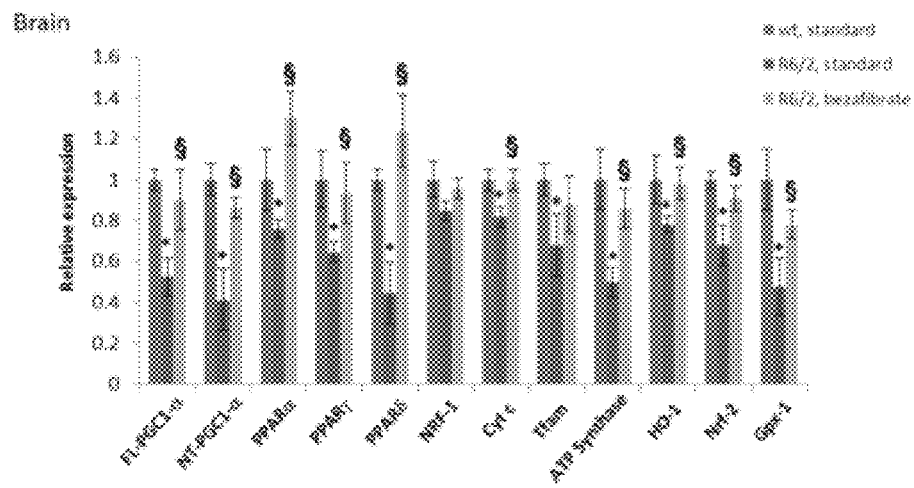
FIG. 1A illustrates a relative expression of full-length (FL) and N-truncated (NT) isoforms of PGC-1α, PPARα, γ, δ, and the downstream target genes, nuclear respiratory factor NRF-1, Cyt c, Tfam, ATP synthase, as well as the oxidative stress response genes HO-1, Nrf-2 and Gpx-1 in brain of R6/2 mice on a standard diet or on the bezafibrate diet. The levels of each gene transcript were normalized to that of β-actin and expressed as fold variation relative to the wild-type mice on a standard diet. The asterisks and symbols represent the significance levels calculated by unpaired, Student's two-tailed t test: *$p<0.05$ compared to the wild-type controls; §$p<0.05$ compared to R6/2 controls. (n=5 and bars represent S.E.M.).
Figure 1B:
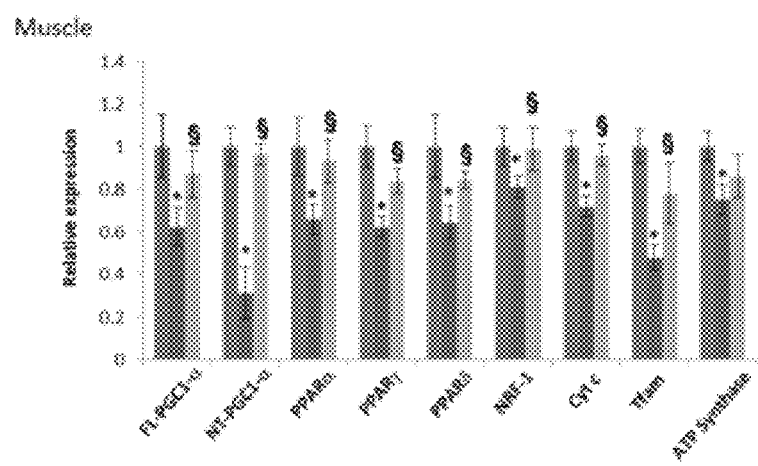
FIGS. 1B and 1C illustrate a relative expression of FL-, NT-PGC-1α, PPARα, γ, δ, NRF-1, Cyt c, Tfam and ATP synthase in muscle (FIG. 1B) or brown adipose tissue (BAT) (FIG. 1C) of R6/2 mice on a standard diet or on the bezafibrate diet. β-actin and wild-type mice on a standard diet were used as reference.
Figure 1C:
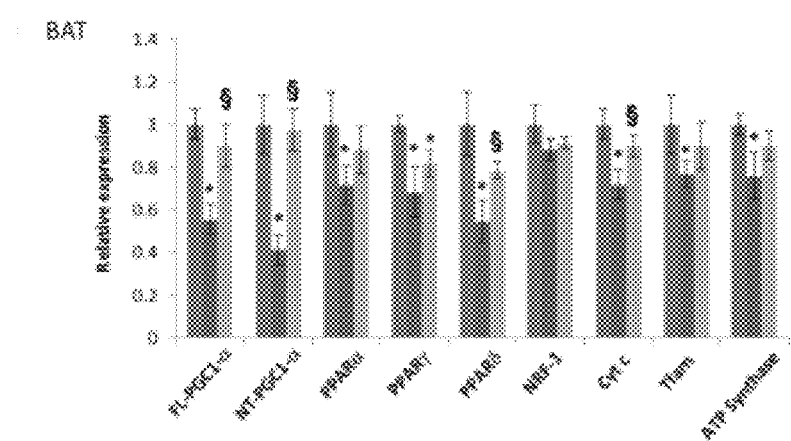

R6/2 mice with an N-terminal genomic fragment containing exon 1 with approximately 130 CAG repeats (Mangiarini et al. 1996) were utilized. R6/2 mice and their wild-type littermates were raised on a diet containing 0.5% bezafibrate or standard chow, starting right after weaning. Quantitative real-time PCR analysis revealed that both the full-length (FL) and N-truncated (NT)-isoforms of PGC-1α are down-regulated in R6/2 mice brain, muscle and brown adipose tissue (BAT) compared to their wild-type littermates (FIGS. 1A-1C). Both FL and NT-PGC-1α isoforms were significantly induced in the brain and peripheral tissues of R6/2 mice that were fed the bezafibrate diet, and their levels were not significantly different from those of the wild-type controls. The ability of PGC-1α to activate a diverse set of metabolic programs in different tissues depends on its ability to form heteromeric complexes with a variety of transcription factors, including nuclear respiratory factor-1 (NRF-1) and PPARs. PPAR-γ and PPAR-6, are co-activated with PGC-1α in a positive feedback loop, and regulate glucose metabolism, fatty acid oxidation and mitochondrial biogenesis (Hondares et al 2006; Huss and Kelly 2004). The mRNA expression levels of the three isoforms of PPARs (α, γ and 6) and that of Cytochrome c (Cyt c), Tfam, ATP synthase were lower in the R6/2 brain, muscle and BAT as compared to their wild-type littermates, however, levels of NRF-1 were unchanged in brain and BAT. Bezafibrate administration restored the mRNA levels of PGC-1α, PPARs and downstream targets of PGC-1α, Cyt c, Tfam and ATP synthase in brain, muscle and BAT of R6/2 mice (FIGS. 1A-1C).

Concomitant with the stimulation of expression of genes involved in mitochondrial energy production, PGC-1α also induces genes responsible for countering reactive oxygen species (ROS) generated as by-products of oxidative metabolism (St-Pierre et al. 2006; Lin et al 2005). In R6/2 brains, we found that genes responsive to ROS, such as, hemoxygenase-1 (HO-1), Nuclear factor (erythroid-derived 2)-like 2 (Nrf-2) and Gpx-1 were significantly downregulated, and bezafibrate restored the levels of these genes to control levels in the R6/2 mice (FIGS. 1A-1C).

Improved Behavior and Survival in R6/2 Mice Treated with Bezafibrate

To assess muscle strength we tested the R6/2 mice and their wild-type littermates on the grip strength test (FIG. 2A). As reported previously, R6/2 mice showed a robust deterioration of their grip strength as they aged, compared to their wild-type littermates with differences being significant at 8, 10 and 12 weeks of age (Menalled et al. 2009). Bezafibrate treated R6/2 mice showed an increase in grip strength (up to 2 fold) compared to the untreated R6/2 mice (FIG. 2A). To further assess motor function, general activity and exploration, mice were tested in the open field test. R6/2 transgenic mice were significantly hypoactive, as measured by the total distance covered, and in the bezafibrate treated R6/2 group, a significant amelioration of the deficit was seen. The total distance covered was significantly greater in the treated group than in the R6/2 mice on a standard diet (FIG. 2B). Motor coordination was assessed by performance on an accelerated rotarod apparatus. Latency to fall was recorded for 3 trials per weekly assessment and scores were averaged (FIG. 2C). Consistent with previous literature, R6/2 mice showed progressive, robust deficits on rotarod, with a significantly reduced latency to fall starting at 6 weeks of age (Menalled et al. 2009). Bezafibrate treated mice remained on the rotarod longer than the untreated R6/2 mice, indicating better motor coordination in the treated mice (FIG. 2C).

R6/2 mice normally die prematurely as compared to their wild-type littermates, between the age of 70-91 days (Mangiarini et al. 1996). Symptomatic mice approaching the disease endstage were examined twice daily (morning and late afternoon) to assess when they reached end-stage of the disease, as assessed by the righting reflex or failure to eat moistened chow placed beside mice over a 24 hour period. At this point, mice were euthanized by CO2 inhalation. This day was recorded as time of death of the mice. FIG. 2D shows a Kaplan-Meier plot of the survival of R6/2 mice. In our hands, the R6/2 mice survived to 77-88 days of age, and the longest living mouse died at 90 days of age (mean=84+ 1.2 days). Bezafibrate treated R6/2 mice lived 20% longer than the R6/2 mice on a standard diet (mean=102+3.2 days) (FIG. 2D).

Bezafibrate Rescues Neuropathological Features in R6/2 Mice

The neuropathological features of HD are general atrophy of the brain, with losses of projection neurons in the deeper layers of the cortex and calbindin immunoreactive medium spiny neurons (MSNs) in the caudate-putamen (Vonsattel and DiFiglia 1998). A stereological analysis of calbindin-immunoreactive medium spiny neuronal perikarya was performed in the striatum of 12-week-old R6/2 mice. Consistent with other studies, a reduction of neuron size was found in R6/2 mice as compared to wild-type controls (FIG. 3A), (Ferrante et al 2002). Induction of PGC-1α expression by bezafibrate treatment was accompanied by increases in the calbindin-positive neuron area in the R6/2 mice (FIGS. 3A-3C,4).

The striatum of R6/2 mice treated with bezafibrate and those on standard diet were further examined at the ultrastructural level. Several apoptotic neurons with condensed cytoplasm and abnormal nuclear shape showing margination and condensation of chromatin were observed (FIG. 3B, quadrants a and b). Enlarged extracellular spaces, cytoplasmic vacuoles and lysosome-like dense bodies were also noted. Moreover, degenerated or degenerating mitochondria could also be seen. Ultrastructural abnormalities in the brains of HD mice have previously been noted, including the presence of dark neurons and abnormally shaped nuclei (Davies et al 1997; Yu et al 2003). In the bezafibrate treated R6/2 mice, amelioration of these abnormalities was noted. In particular, in the striata from bezafibrate treated R6/2 mice, the cytoplasm of the neurons is preserved, and the axonal and dendritic profiles in the neuropil are relatively intact (FIG. 3B, quadrants c and d). Mitochondrial density was also measured. For this purpose, the intact mitochondria count per cell was noted and divided by the area of the cytoplasm, yielding the mitochondrial density (FIG. 3C). Several neurons were counted per animal and a group average is presented in FIG. 3C. A significant increase in numbers of mitochondria in the striata of bezafibrate treated R6/2 mice was seen, as compared to the R6/2 mice on standard chow.

Glial fibrillary acidic protein (GFAP) immunostaining identifies reactive gliosis, an early marker of CNS damage in HD (35). GFAP staining was compared in the striatum of bezafibrate treated and untreated wild-type and R6/2 mice (FIG. 5). Compared with age-matched wild-type mice striatum, the striatum of R6/2 mice showed a remarkable increase in GFAP immunoreactivity, indicated by intense labeling throughout astroglial cell bodies and their fibrous processes and the presence of hypertrophied astrocytes (inset). An amelioration of astrogliosis was observed in striata of R6/2 mice treated with bezafibrate (FIG. 5).

Evidence for Amelioration of Oxidative Stress in R6/2 Mice Treated with Bezafibrate In HD, the generation of ROS and the resulting oxidative stress, are implicated in the neurodegeneration and neuronal death (Browne et al 1997; Reviewed in Stack et al 2008). Postmortem human HD brain tissue shows increased levels of oxidative damage markers, including increased cytoplasmic lipofuscin, DNA strand breaks, oxidized DNA bases, protein nitration, carbonyls and lipid oxidative damage. Levels of malondialdehyde (a marker for oxidative damage to lipids), are elevated in human HD striatum and cortex as compared with age-matched controls (Browne et al 1997). Increased immunoreactivity for MDA was observed in R6/2 striatum, which was ameliorated by the bezafibrate diet (FIG. 6A). Consonant with the immunohistochemical data, HPLC analysis also revealed elevated levels of MDA in R6/2 brains which were significantly reduced with bezafibrate treatment (FIG. 6B).

Bezafibrate Prevents the Fiber-Type Switching and Structural Abnormalities in Muscle Muscle fibers can be classified as 'slow-twitch' fatigue resistant fibers which are dependent on PGC-1α, and contain numerous mitochondria and use oxidative phosphorylation to generate ATP (type I and IIA fibers), and 'fast-twitch fatiguable' fibers (type IIX and IIB fibers), which have few mitochondria and which utilize glycolysis to generate ATP (Lin. et al. 2002). PGC-1α levels are normally high in muscle enriched with type I fibers, such as the soleus muscle, and very low in type II fiber rich muscles such as the extensor digitorum longus and the gastrocnemius (Lin. et al. 2002). The soleus muscle of R6/2 mice and their wild-type littermates for fiber typing were examined using succinate dehydrogenase (SDH) histochemistry (FIG. 7A). There was reduced SDH staining in the soleus of R6/2 mice on a standard diet. Quantitation of the SDH histochemistry revealed a significant reduction of type I fibers, and an increase in type II fibers in the soleus muscle of R6/2 mice, consistent with the reduced expression of PGC-1α. A reversal of this fiber-type switching was seen in R6/2 mice on the bezafibrate diet, with the type I and II fibers returning back to normal levels seen in wild-type mice (FIG. 7B).

Further studies to determine the effects of bezafibrate on mitochondrial area and mitochondrial number were carried out using electron microscopy. In wild-type mice, mitochondria are uniform in size and align regularly along the Z lines (FIG. 7C and FIG. 9), whereas in the R6/2 mice, the mitochondria are irregular in shape and poorly aligned. Similarly, PGC-1α-deficient mice show fewer and smaller mitochondria in soleus muscle (Leone et al. 2005). In the R6/2 mice treated with bezafibrate, mitochondria appeared to be of normal shape and their arrangement along the Z-lines was restored to normal (FIG. 7C).

Bezafibrate Attenuated Vacuolization in the Brown Adipose Tissue of R6/2 Mice

Using other mouse models of HD, (N171-82Q and NLS-N171-82Q HD mice), it was previously reported that HD mice have an impaired response to cold temperature, i.e. defective adaptive thermogenesis (Weydt et al. 2006; Chaturvedi et al 2010). In rodents, brown adipose tissue (BAT) is the principal tissue that mediates the adaptive thermogenesis, and is distinguished from white fat by its high degree of vascularization and mitochondrial density (Cannon and Nedergaard 2004). PGC-1α is expressed in BAT and is a key mediator of adaptive thermogenesis by activating uncoupling protein 1 (Puigserver et al 1998). As seen with the other HD mice models, the H&E staining of BAT from the R6/2 mice showed marked reductions in cell density and nuclei numbers and increased vacuolization when compared with wild-type mice (FIG. 8). The white-fat like appearance of BAT was due to accumulation of neutral lipids as revealed by Oil red O staining (FIG. 8, inset). Bezafibrate reduced vacuolization in the brown adipose tissue of the R6/2 transgenic mice as compared to R6/2 mice fed a standard diet, and reduced oil red O staining was also observed (FIG. 8).

Discussion of HD Work

A number of bioenergetic and metabolic impairments are known to occur in HD patients: 1) increased lactate production in cerebral cortex and basal ganglia; 2) reduced phosphocreatine to inorganic phosphate ratio in resting muscle, the extent of which correlates with CAG repeat expansion length, and which is exacerbated after exercise; 3) abnormal mitochondrial membrane depolarization in lymphoblasts; 4) impaired complex II, III and IV activity of the mitochondrial oxidative phosphorylation pathway and reduced aconitase activity in the basal ganglia; 5) abnormal ultrastructure of mitochondria in cortical biopsies obtained from patients with both juvenile and adult-onset HD; and 6) pathologic grade dependent reductions in numbers of mitochondria (Kim et al 2010); Reviewed in Browne and Beal 2004). Literature shows that the phenotypic and neuropathologic features of HD can be modeled in rodents and primates, with the mitochondrial toxin 3-nitropropionic acid (Beal et al 1993; Brouillet et al 1995).

Impaired expression and/or function of PGC-1α, the master co-regulator of mitochondrial biogenesis, has been implicated in the pathogenesis of several neurodegenerative disorders, including Parkinson's disease, Alzheimer's disease, Friedreich's ataxia, and HD. A link of the transcriptional coactivator PGC-1α to HD pathogenesis was first suggested by observations in PGC-1α-deficient mice (Lin et al. 2004; Leone et al. 2005). PGC-1α knockout mice exhibit impaired mitochondrial function, a hyperkinetic movement disorder and striatal degeneration, all features also observed in HD (Lin et al. 2004; Leone et al. 2005). Furthermore, impaired PGC-1α function and levels occur in striatal cell lines, transgenic mouse models of HD and in postmortem brain tissue from HD patients (Cui et al 2006; Weydt et al. 2006). Recent studies showed that expression of mutant htt in primary oligodendrocytes results in decreased expression of PGC-1α, and decreased expression of myelin basic protein (MBP) and deficient myelination were found in the R6/2 mouse model of HD (Xiang et al. 2011). A decrease in MBP and deficient postnatal myelination occurs in the striatum of PGC-1α knockout mice (Xiang et al. 2011). In accordance with earlier studies, the PGC-1α signaling pathway is shown to be downregulated in the brain, muscle and brown adipose tissue of R6/2 HD mice. Spongiform lesions in R6/2 striatum, along with the presence of astrogliosis, was also found, which is similar to observations made in PGC-1α-deficient mice (Lin et al. 2004; Leone et al. 2005). The neuropathologic observation of spongiform degeneration is of interest, since similar lesions occur in MnSOD null mice (Hinerfeld 2004), and PGC-1α plays an important role in controlling expression of MnSOD (St-Pierre et al. 2006).

In the present invention, it was found that the impairment of PGC-1α pathway can be reversed in brain, muscle and brown adipose tissue from R6/2 HD mice, using the PPAR-pan-agonist, bezafibrate, which was previously shown to be effective in increasing life span and delaying the onset of symptoms in a mouse model of mitochondrial myopathy (Wenz et al 2008). Wide-spread beneficial effects of bezafibrate on behavior, survival and histopathological features in brain, muscle and BAT of R6/2 mice were found. The increase in survival observed with the bezafibrate diet (20%) is comparable to the highest range of percent increases in survival seen in other therapeutic trials in mouse models of HD (Hersch and Ferrante 2004). It was showed that administration of creatine or triterpenoid compounds to N171-82Q mice increased survival by 19% or 21.9% respectively, and that administration of coenzyme Q10 with remacemide or administration of mithramycin increased survival by 31.8% or by 29.1% in R6/2 mice, respectively (Andreassen et al. 2001; Beal and Ferrante 2004; Ferrante et al. 2004; Stack et al 2010). Bezafibrate, therefore, improves the behavioral phenotype and survival of R6/2 mice in a comparable range to the best therapeutic interventions thus far tested. Recently, administration of a PPARγ agonist, thiazolidinedione, was shown to produce beneficial effects on weight loss, mhtt aggregates and global ubiquitination profiles in R6/2 mice (Chiang et al. 2010). Earlier, it was shown in STHdhQ111 cells, that PPARγ activation by rosiglitazone prevents the mitochondrial dysfunction and oxidative stress that occurred when mutant striatal cells were challenged with pathological increases in calcium (Quintanilla et al 2008).

It was also found that the improved behavioral phenotype, increased survival and the induction of the PGC-1α signaling pathway was accompanied by reduced neuropathological features and a significant increase in mitochondrial density in striatum of R6/2 mice treated with bezafibrate. PGC-1α plays a critical role in mitochondrial biogenesis, and in studies of cortical, midbrain and cerebellar granule neurons, both PGC-1α and PGC-1β control mitochondrial density (Wareski et al 2009). Overexpression of PGC-1β or PGC-1α, or activation of the latter by SIRT1, protects neurons from mutant htt-induced loss of mitochondria and cell death (Wareski et al 2009). The SIRT1 activator, resveratrol, increases the activity of PGC-1α and improves mitochondrial activity as a consequence of its deacetylation of PGC-1α, which increases its effects on liver, fat and muscle metabolism (Lagouge et al. 2006). Recently, it showed that resveratrol treatment of the N171-82Q transgenic mice, produced increased PGC-1α and reduced vacuolization in BAT and reduced glucose levels, but there were no beneficial effects in the striatum due to poor brain penetration (Ho et al 2010).

In disease-free neurons, the generation of ROS is a normal by-product of cellular respiration, mediated by mitochondria. Accumulation of ROS in neurons and subsequent oxidative stress is attenuated by free radical scavengers, such as glutathione and superoxide dismutase, preventing subsequent damage (Browne and Beal 2006; Beal 1999). There is evidence for oxidative damage in HD (Reviewed in Stack et al 2008). Markers of oxidative damage, including heme oxygenase (an inducible isoform that occurs in response to oxidative stress), 3-nitrotyrosine (a marker for peroxynitrite-mediated protein nitration), and malondialdehyde (MDA, a marker for oxidative damage to lipids), are elevated in human HD striatum and cortex as compared with age-matched control brain specimens (Browne et al 1999). The extent and intensity of these markers mirror the dorsoventral pattern of progressive neuronal loss in the neostriatum, with increased immunoreactive expression in the dorsal striatum as compared with the less severely affected ventral striatum. Consistent with the immunohistochemical data, analysis of biochemical assays in HD patients show significant increases in malondialdehyde and 4-hydroxynonenal brain levels, almost 8-fold greater than in control subjects (Stoy et al 2005).

PGC-1α plays a role in the suppression of oxidative stress, and it induces antioxidant enzymes, including copper/zinc superoxide dismutase (SOD1), manganese SOD (SOD2), and glutathione peroxidase (Gpx1) (St-Pierre et al 2006). In concert with the increase in PGC-1α expression, it was observed that the oxidative stress response genes such as hemeoxygenase-1 (HO-1), Nrf-2 and Gpx1 were also increased in the brains of R6/2 mice treated with bezafibrate. The levels of MDA measured by HPLC, and MDA immunoreactivity in striatum were significantly reduced in R6/2 mice by bezafibrate treatment as compared to the control R6/2 mice. These observations provide strong evidence for amelioration of oxidative stress in R6/2 mice by upregulation of PGC-1α using bezafibrate. Recently, it showed that administration of triterpenoids, which activate the Nrf2/ARE transcriptional pathways, are neuroprotective in the N171-82Q transgenic mouse model of HD (Stack et al 2010).

PGC-1α is reduced in muscle from HD transgenic mice and in muscle biopsies and myoblasts from HD patients (Chaturvedi et al 2009). There was an impaired response to guanidinopropionic acid (GPA) treatment, in the muscle and brains of NLS-N171-82Q HD mice. In wild-type mice, GPA treatment activated AMPK, which increased PGC-1α, NRF1 and Tfam, and this was accompanied by an increase in COX II/18s rRNA, consistent with mitochondrial biogenesis, increased mtDNA and increased numbers of mitochondria. This pathway, which leads to an increase in mitochondria in response to an energetic stress, was blocked in the NLS-N171-82Q HD mice (Chaturvedi et al. 2009; Chaturvedi et al 2010). Bezafibrate treatment in R6/2 mice rescued the PGC-1α signaling pathway and restored the levels of downstream target genes involved in mitochondrial function, e.g., cytochrome c, Tfam and ATP synthase. Bezafibrate also reversed the fiber type switching back to normal and restored the normal morphology of muscle, shape, numbers and arrangement of mitochondria along the Z-lines in the soleus muscle of R6/2 mice.

PGC-1α is rapidly induced in response to cold exposure and regulates key components of adaptive thermogenesis including the uncoupling of respiration via uncoupling proteins (UCP-1), resulting in heat production in brown adipose tissue (BAT). Significant hypothermia at both baseline and following cold exposure was found in both N171-82Q and R6/2 HD mouse models (Weydt et al. 2006). Following cold exposure, UCP-1 expression is decreased in BAT from N171-82Q transgenic HD mice relative to wild type controls. In brown fat adipocytes, there are reduced ATP/ADP ratios and mitochondrial numbers, similar to the findings in PGC-1αKO mice (Lin et al. 2004; Leone et al. 2005). Similar to previous findings, it was also observed that in BAT of the R6/2 mice, there is a marked vacuolization, which is due to accumulation of neutral lipids. Bezafibrate reduced the vacuolization and oil red O staining in the BAT of R6/2 mice, indicating amelioration of neutral lipid accumulation.

The important role of PGC-1α in the regulation of mitochondrial function, together with the association of mitochondrial dysfunction with HD pathogenesis, implies that activation of PGC-1α may be useful in the treatment of HD. In the present invention, it shows that stimulation of PPAR-PGC-1α axis by bezafibrate produces wide-spread beneficial effects in brain and peripheral tissues of R6/2 model of HD. Bezafibrate is an attractive agent for clinical studies since it has been used in man for more than 25 years, and it is well-tolerated with few side effects. It is therefore particularly attractive for clinical trials in neurodegenerative diseases such as HD. In other work, it found that bezafibrate exerts beneficial effects in BACHD mice, a full length mhtt transgenic mouse model of HD (Gray et al. 2008; Johri and Beal, unpublished observations). The present invention showing beneficial effects of bezafibrate in the R6/2 mouse model of HD, provides strong evidence that bezafibrate can be proved to be an effective neuroprotective agent for treatment of HD.

Example 2

Bezafibrate's Effects on Tauopathy Materials and Methods for Tauopathy Work

Animals and Treatment

Animals were generated by breeding P301S transgenic male mice with wild-type female mice obtained from Jackson Laboratory (Bar Harbor, Me., USA). Offspring were genotyped by PCR of tail DNA. P301S transgenic mice and their wild-type littermates were randomly assigned to receive either control diet (LabDiet 5002) or 0.5% bezafibrate diet (Sigma, St. Louis, Mo., USA) from 1 to 10 months of age ad libitum. The chow was pelleted by Purina-Mills (Richmond, Ind., USA). Behavioral analyses were performed at 5, 7, and 9 months of age. Histopathological and biochemical analyses were conducted at 10 months of age on the same animals. All experiments were approved by the Weill Cornell Medical College Institutional Animal Care and Use Committee.

Behavior

One week prior to behavioral testing, the experimenter handled the mice daily in order to habituate them. Body weights were recorded every month from 2 to 9 months of age. Locomotor activity and exploration were assessed in the openfield as previously described (Dumont et al 2010). Briefly, mice were placed in the apparatus for a 5 min trial. Distance traveled and rearing frequency were recorded using a video tracking system (Ethovision 3.1, Noldus Technology, Attleborough, Mass., USA). As an indicator of exploration and anxiety, the time spent in the periphery and the center of the apparatus was recorded. Grip strength was measured using the grid test. Animals were placed on a metal wire grid (10 cm×5 cm, height: 30 cm) that was inverted after a few seconds. Latency to fall was recorded during a 3 min trial. Motor coordination was assessed using the accelerated rotorod during which latency before falling was recorded. Mice were placed on the rotating beam for 3 trials per day over 3 days. Acceleration was set at 0.3 rpm/sec over 2 min (4 to 40 rpm).

Western Blotting

After behavioral testing, half of the mice in each group were sacrificed by decapitation. Tissues were collected, dissected, snap frozen in liquid nitrogen, and stored at −80° C. for biochemical studies. Tissues were homogenized in RIPA buffer with protease and phosphatase inhibitors (Santa Cruz Biotechnology, Santa Cruz, Calif., USA). Equal amounts of protein were electrophoresed through 4-12% Tri-Bis NuPage gels (Invitrogen, Carlsbad, Calif., USA). After transfer to polyvinylidene fluoride (PVDF), membranes were blocked in 5% non-fat dry milk in phosphate buffer saline with 0.05% Tween 20 (PBST) and exposed overnight to the primary antibody at 4° C. Horseradish peroxidase-conjugated (HRP) secondary antibody binding was visualized with enhanced chemiluminescence (Pierce, Rockford, Ill., USA).

Primary antibodies and concentrations used for western blotting were: DA9 mouse monoclonal anti-total tau (aa102-140) (1:1,000, gift from Dr. Peter Davies); mouse monoclonal anti-GSK3β (1:500, Abcam, Cambridge, Mass., USA); rabbit monoclonal anti-phospho-GSK3β (Ser9) (1:1,000, Cell Signaling, Danvers, Mass., USA); rabbit monoclonal p70S6K (1:1,000, Cell Signaling, Danvers, Mass., USA); rabbit monoclonal anti-phospho-p70S6K (Thr389) (1:1,000, Cell Signaling, Danvers, Mass., USA); rabbit polyclonal anti-LC3 (1:2,000, Cell Signaling, Danvers, Mass., USA); mouse monoclonal anti-PGC1α (1:200, Calbiochem, San Diego, Calif., USA); rabbit polyclonal anti-COX2 (1:200, Abcam, Cambridge, Mass., USA); mouse monoclonal anti-NRF1 (1:200, Abcam, Cambridge, Mass., USA); mouse monoclonal anti-porin (VDAC) (1:3,000, Invitrogen, Carlsbad, Calif., USA); mouse monoclonal anti-nitrotyrosine (1:250, Abcam, Cambridge, Mass., USA); and mouse monoclonal anti-β-actin (1:10,000, Sigma, St. Louis, Mo., USA). Quantitative analysis was performed using NIH-based "Scion Image" software. Statistical analysis was performed using ratios of the densitometric value of each band normalized to β-actin as loading control.

Immunohistochemistry, Immunofluorescence, and Histology

The remaining mice from each group were deeply anesthetized using sodium pentobarbital and transcardially perfused with ice-cold 0.9% sodium chloride and 4% paraformaldehyde. Tissues were collected, dissected, post-fixed in 4% paraformaldehyde followed by gradient sucrose (15% and 30%), and stored in cryoprotectant for immunohistochemical studies. Sections were cut at 50 μm thickness and stained with the following antibodies: MC1 mouse monoclonal anti-human tau (N terminal conformational change, Exon 10) (1:500, gift from Dr. Peter Davies); AT8 mouse monoclonal anti-human tau pSer202/Thr205 (1:500, Thermo Fisher Scientific, Rockford, Ill., USA); rat monoclonal anti-CD11b (1:1,000, AbD Serotec, Raleigh, N.C., USA); rabbit polyclonal anti-GFAP (1:1,000, Dako, Carpinteria, Calif., USA); mouse monoclonal anti-PGC1α (1:200, Calbiochem, San Diego, Calif., USA); rabbit polyclonal anti-nitrotyrosine (1:100, Millipore, Billerica, Mass., USA); rabbit polyclonal anti-cathepsin D (1:1, Biogenex, San Ramon, Calif., USA); rabbit polyclonal anti-LAMP1 (1:100, Abcam, Cambridge, Mass., USA); and rabbit monoclonal anti-MDA (1:1,000, gift from Dr. Craig Thomas). Immunolabeling was detected by the streptavidin-horseradish peroxidase method and visualized after diaminobenzidine (DAB) incubation (Vector, Burlingame, Calif., USA). Quantification was done using five 50 μm serial non-adjacent sections per animal (300 μm apart, from bregma −1.34 through bregma −2.84). The percentage area occupied by AT8 and CD11b, and the number of MC1-positive neurons were measured. Perfused and fixed brown adipose tissues were cut at 16 μm thickness and mounted on slides. Sections were processed for hematoxylin-eosin, and PGC1α stainings.

Gene Expression by qRT-PCR

Fresh frozen tissues stored at −80° C. were processed for RNA extraction (Qiagen kit, Valencia, Calif., USA). Quantitative real-time PCR (qRT-PCR) was performed at the Weill Cornell Medical College Microarray Core Facility using SyberGreen assays with the ABI Prism 7900HT sequence detection system (Applied Biosystems, Foster City, Calif., USA). The following genes were analyzed: PGC1α, NRF1, Tfam, and GAPDH as control.

Mitochondria Characterisation

Sample Preparation

Dissected, non-perfused frontal lobe samples (~30-55 mg) were stored frozen at ¬80° C. until assaying. Before assays, tissue samples were thawed on ice and homogenized with Dounce-type 2 ml homogenizer (glass vessel/glass pestle). The homogenate was centrifuged at 1,000 g×5 min to get rid of nuclear fraction and cell debris; the resulting supernatant was centrifuged at 14,000 g×5 min. The pellet was collected and centrifuged again at 14,000 g×5 min; the final pellet obtained in this step was resuspended in 20 mM HEPES (pH 7.8) and used for all assays.

Immunoblot Analysis—Mitochondria-Enriched Fraction

The protein lysates containing equal amounts of protein were separated by SDS-PAGE, electroblotted onto a nitrocellulose membrane (BioRad, Hercules, Calif., USA), and immunoreacted with an appropriate primary antibody (see below) followed by HRP-conjugated secondary antibody (Kierkegaard Perry Labs Inc., Gaithersburg, Md., USA). Immunoreactive proteins were visualized by incubating blots in chemiluminescence substrate (Pierce, Rockford, Ill., USA). Quantitative analysis was performed using NIH "ImageJ" software. Statistical analysis was performed using ratios of the densitometric value of each band normalized to β-actin as loading control.

Assays

All samples were assayed for the following: complex I activity (NADH:CoQ reductase, rotenone-sensitive (Degli Esposti et al 1993)), complex I subunit expression (immunoblotting with anti-complex I subunit NDUFB8 1:1,000, Invitrogen, Carlsbad, Calif., USA), complex III subunits expression (immunoblotting with anti-Complex III Core 2 subunit UQCR2/QCR2 1:1,000, Invitrogen, Carlsbad, Calif., USA), complex IV subunit expression (immunoblotting with anti-complex IV MT-001 subunit 1:1,000, Invitrogen, Carlsbad, Calif., USA), ATPase subunit expression (immunoblotting with anti-ATPase ATP5A1 subunit 1:1,000, Invitrogen, Carlsbad, Calif., USA), catalase expression (immunoblotting with anti-catalase 1:1,000, Abcam, Cambridge, Mass., USA), cytochrome C content by quantitative ELISA ("Rat/Mouse Cytochrome c Quantikine ELISA Kit", R&D Systems, Minneapolis, Minn., USA), succinate dehydrogenase activity (succinate:CoQ:DCIP reductase, TTFA-sensitive (Arrigoni and Singer 1962)), citrate synthase activity (Srere 1969), aconitase activity ("Aconitase Assay Kit", Cayman Chemical, MI, USA), protein carbonyls by DNP derivatization ("Oxyblot" kit, Cayman Chemical, Ann Arbor, Mich., USA), glutathione reductase activity ("Glutathione Reductase Assay Kit", Cayman Chemical, Ann Arbor, Mich., USA), superoxide dismutase activity ("Superoxide Dismutase Assay Kit", Cayman Chemical, Ann Arbor, Mich., USA). All activities and content values were normalized by protein content (BCA protein assay, Thermo Scientific, FL, USA) and (when appropriate) by citrate synthase activity.

High Performance Liquid Chromatography (HPLC)

The HPLC determination of MDA was carried out by a method modified from a previous report by Agarwal and Chase in 2002 (Agarwal and Chase 2002). Fresh tissues were homogenized in 40% ethanol solution. 50 µl of sample homogenate or MDA standard were prepared in 40% ethanol. 50 µl of 0.05% butylated hydroxytoluene (BHT), 400 µl of 0.44 M H3PO4, and 100 µl of 0.42 mM 2-thiobarbituric acid (TBA) were added to each. Samples were then vortexed, heated for 1.5 hr at 100° C., and immediately cooled with ice water to stop the derivative reaction. MDA-TBA derivative was extracted by adding 250 µl n-butanol, followed by vortexing and centrifugation. 50 µl of n-butanol extract was used for the HPLC assay. The HPLC mobile phase used acetonitrile buffer (20:80, v/v, buffer 50 mM KH2PO4, pH 6.8). The column was an ESA 150×3 mm C18 column with particle size of 3 µm (ESA, Inc., Bedford, Mass., USA). Fluorescence detectors were set at an excitation wavelength of 515 nm and emission wavelength of 553 nm. MDA was eluted in 2 min. Data were normalized by protein content (Biorad Protein Assay Kit, Hercules, Calif., USA).

Statistical Analysis

ANOVA was used to compare all four experimental groups. Post-hoc Fisher's PLSD tests were used for further comparison. Two-tailed unpaired t-tests were used when only two groups were analyzed (P301S mice fed control diet and P301S mice fed bezafibrate diet) (Statview 5.0.1, SAS Institute Inc., Cary, N.C., USA). All presented data were expressed as means±standard errors of the means.

Results for Tauopathy Work

Bezafibrate Treatment Rescued Behavioral Abnormalities in P301S Mice

In the openfield, P301S mice were hyperactive relative to their wild-type littermates at 5, 7, and 9 months of age (FIGS. 14 and 15). P301S mice were also disinhibited as evidenced by the increased time spent in the central area of the apparatus (FIG. 16). Both locomotor and anxiety-related abnormalities were rescued after bezafibrate treatment in P301S mice. No differences were found between wild-type groups with or without the treatment.

Figure 17A:
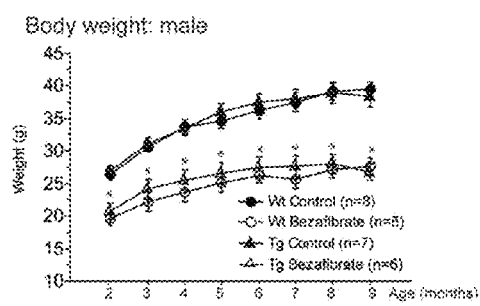
Figure 17B:
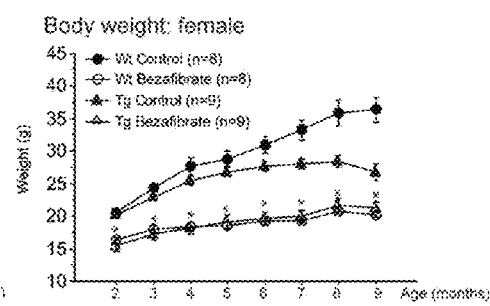

Bezafibrate treatment reduced body weight in both P301S and wild-type mice (FIGS. 17A and 17B). Bezafibrate treated mice also had increased latency to fall from the grid and the rotorod as compared to control treated mice.

Bezafibrate Treatment Also Reduced Tau Pathology in P301S Mice

To assess tau phosphorylation and accumulation in the brain of P301S mice, two antibodies, AT8 (anti-human tau pSer202/Thr205) and MC1 (anti-human tau, N-terminal conformational change, Exon 10) were used. In 10 month-old P301S mice, tau pathology was markedly increased in the cortex and hippocampus compared to their wild-type littermates (FIGS. 10A-10D). After bezafibrate treatment, AT8 and MC1 immunoreactivities in the cortex and hippocampus were diminished. This indicates that bezafibrate reduced both tau phosphorylation (FIGS. 11A-D) and neurofibrillary tangle formation in brains of P301S mice. Levels of AT8 were also measured in the spinal cord of P301S mice, and a trend toward a decrease in AT8 immunoreactivity was found after bezafibrate treatment.

In addition, using DA9 antibody (normal total tau), it was found that bezafibrate treatment did not alter levels of normal tau in P301S mice. Expression levels of normal total tau remained unchanged in P301S mice fed bezafibrate diet relative to P301S mice fed control diet.

Bezafibrate Decreased Phospho-GSK3/3 Expression and Induced Tau Degradation

The expression of glycogen synthase kinase-3-beta (GSK3β) was studied in order to investigate the mechanism by which bezafibrate reduced tau hyperphosphorylation. GSK3β is a well-known serine/threonine protein kinase that mediates the addition of phosphate molecules in cellular substrates such as the protein tau (Hernandez et al 2009; Plattner et al 2006; Soutar et al 2010). By western blotting, we observed that administration of bezafibrate significantly decreased levels of phospho-GSK3β in P301S mice (FIGS. 11A-11D).

In addition, whether bezafibrate could induce lysosomal and autophagic pathways in order to facilitate tau degradation was investigated. To study lysosomes, brain sections were stained with the mature form of cathespin D and with lysosomal-associated membrane protein 1 (LAMP1). In P301S mice, bezafibrate treatment increased cathepsin D and LAMP1 immunoreativity. Co-staining of AT8 and LAMP1 revealed that in bezafibrate treated P301S brains, AT8 staining was reduced. It also found that where LAMP1 staining was increased, AT8 staining was not present.

Levels of phospho-p70S6K (another serine/threonine protein kinase) were reduced after bezafibrate treatment, suggesting that the treatment may have induced autophagy via the mammalian target of rapamycin pathway (mTOR). To further establish an effect of bezafibrate on autophagy, we measured levels of LC3 by western blotting. During autophagy, LC3 I (the cytoplasmic form of LC3) is recruited by autophagosomes and converted to LC3 II (the membrane bound form of LC3). Administration of bezafibrate did not alter levels of LC3 I, but increased levels of LC3 II in P301S mice, suggesting the presence of autophagic activation.

Bezafibrate Had Anti-Inflammatory Effects in P301S Mouse Brains

Previous reports demonstrated that P301S mice develop early microglial activation as compared to their wild-type littermates (Yoshiyama et al 2007; Bellucci et al 2004). In this study, increased microglial activation was observed in 10 month-old P301S mice relative to non-transgenic littermates, as evidenced by the elevated CD11b immunoreactivity). Moreover, it was found that bezafibrate treatment significantly decreased the percentage area covered by CD11b immunoreactivity in the hippocampus of P301S mice. No differences were seen in the cerebral cortex or the spinal cord (data not presented). Levels of cyclooxygenase 2 (COX2) were also measured, and found increased in P301S mice as compared to their wild-type littermates. Bezafibrate reduced the COX2 levels in P301S mice, consistent with an anti-inflammatory response. Levels of GFAP were also assessed the in the hippocampus, and it was found that they were reduced by bezafibrate treatment in the P301S mice, and their wild-type littermates. Under control conditions, the levels of GFAP were not significantly different between groups.

Bezafibrate Reduced Oxidative Stress in the Spinal Cord by Activating the PGC1α Pathway The oxidative stress markers malondialdehyde (MDA) and nitrotyrosine were analyzed in both the brain and spinal cord of P301S mice. In P301S brains, increased MDA or nitrotyrosine relative to wild-type brains were not found. Consistent with this data, no effect of bezafibrate on mitochondrial enzymes and PGC1α was observed except that complex I level was increased in wild-type mice fed bezafibrate diet relative to wild-type mice fed control diet. However, in P301S spinal cords, there was an increase of lipid peroxidation and protein nitration as compared to wild-type littermates. No differences were found between the wild-type groups with or without bezafibrate treatment. Both MDA levels and immunoreactivity and nitrotyrosine levels and immunoreactivity were elevated in the P301S mice. Bezafibrate treatment significantly rescued MDA and nitrotyrosine levels back to wild-type levels in the spinal cord.

As a mechanism of action, bezafibrate could activate the peroxisome proliferator-activated receptor gamma coactivator 1 alpha (PGC1α) pathway, as a mechanism of action. Therefore, the expression of PGC1α and its downstream targets were studied. It was found that after bezafibrate treatment, expression of PGC1α and nuclear respiratory factor 1 (NRF1) were increased in P301S mice. Mitochondrial voltage-dependent anion channels (VDAC) were also elevated, consistent with an increase in mitochondrial biogenesis.

Bezafibrate Improved Brown Adipose Pathology by Activating the PGC1α Pathway

Hematoxylin-Eosin staining was used to study vacuolation in the brown adipose tissue of P301S mice. It was found that P301S mice had increased vacuolation compared to their wild-type littermates. No differences were detected between wild-type mice with or without bezafibrate. After bezafibrate treatment, brown adipose pathology was much improved in the P301S mice.

To determine the mechanism by which bezafibrate rescued vacuolation, gene expression of the PPAR downstream targets, such as PGC1α, nuclear respiratory factor 1 (NRF1), and transcription factor A mitochondria (Tfam) were assessed. It was found that PGC1α expression was decreased in P301S mice relative to their wild-type littermates. Administration of bezafibrate increased gene expression of PGC1α, NRF1, and Tfam. In wild-type mice fed the bezafibrate diet, Tfam and NRF1 expressions were also increased as compared to wild-type mice fed control diet. In addition, the distribution of PGC1α in the brown fat was studied by immunohistochemistry. In P301S mice, PGC1α immunoreactivity was localized at the periphery of enlarged lipid droplets. After bezafibrate treatment, the size of lipid droplets was reduced and PGC1α immunoreactivity was more diffuse in the cytoplasm as seen in wild-type mice.

Discussion of Tauopathy Work 0.5% bezafibrate was administered in the diet to P301S mice and their wild-type littermates from 1 to 10 months of age. P301S mice are a mouse model of tauopathy based on a mutation which causes fronto-temporal dementia in man. The P301S mice show early synaptic deficits and inflammation as well as a progressive tau pathology and neurodegeneration (Yoshiyama et al 2007). The effects of bezafibrate on behavior, tau phosphorylation and accumulation, mitochondrial function, oxidative stress, and inflammatory markers were assessed.

It was found that bezafibrate rescued behavioral abnormalities. It also reduced tau phosphorylation and neurofibrillary tangle formation by inhibiting glycogen synthase kinase 3 beta (GSK3β) and enhancing tau degradation. In addition, bezafibrate decreased glial activation by acting on cyclooxygenase 2. In the spinal cord, bezafibrate reduced oxidative stress by upregulating the peroxisome proliferator-activated receptor gamma coactivator 1 alpha (PGC1α) pathway. Considering the importance of PGC1α in mitochondrial biogenesis, the brown adipose tissue of P301S mice was examined. P301S mice had increased vacuolation and reduced PGC1α expression. Bezafibrate treatment improved brown fat pathology by upregulating the PGC1α pathway and its downstream targets. Therefore, it was demonstrated that the pan-PPAR agonist bezafibrate is protective in P301S transgenic mice through specific PPAR related mechanisms, suggesting an important role of these pathways in models of tauopathy.

Bezafibrate reduced the body weights of both P301S mice and their wild-type littermates. In a study on wild-type mice fed a high glucose, high fat diet, bezafibrate improved body weight, glucose intolerance, and insulin sensitivity (Fernandes-Santos et al 2009). Bezafibrate was surprisingly more potent than agonists of PPARα (fenofibrate) or PPARγ (rosiglitazone) agonist alone (Fernandes-Santos et al 2009). The effects on lowering body weight also explain the improvement of performance found in the grid and accelerating rotorod tests in P301S mice and their wild-type littermates. For all other measurements, bezafibrate did not produce any effects in wild-type treated mice. P301S mice are known to be hyperactive as compared to non-transgenic mice (Scattoni et al 2010). In the present invention, it was found that bezafibrate treatment rescued this hyperactivity as well as disinhibition what was seen at 5, 7, and 9 months of age.

Interestingly, the data showed that after bezafibrate administration, levels of AT8 and MC1 immunoreativity were significantly decreased in the brains of P301S mice. This data indicates that bezafibrate reduced tau hyperphosphorylation and neurofibrillary tangle formation. In the spinal cord, there was a trend toward a decrease in tau hyperphosphorylation after bezafibrate treatment. The reduction of tau phosphorylation could be explained by decreased levels of phospho-GSK3β, which were observed with bezafibrate treatment. Whether bezafibrate enhanced tau degradation was also investigated. It was found that bezafibrate treatment increased cathepsin D and LAMP1 immunoreactivity, suggesting an increase in lysosomal function and autophagy. Although they were not co-localized, co-staining of AT8 and LAMP1 revealed that after bezafibrate treatment, AT8 immunoreactivity was reduced while LAMP1 immunoreactivity was elevated. Interestingly, where LAMP1 staining was increased, AT8 staining was not present, suggesting that tau may have been eliminated. Previous reports have demonstrated that tau and other proteins can be degraded by the lysosomal system (Bahr 2009) and conversely that deficiency of the lysosomal system induces protein accumulation (Khurana et al 2010).

Additionally, in cancer cells, PPARγ agonists were shown to induce autophagy (Zhou et al 2009). According to Zabirnyk and colleagues, the induction of autophagy by PPARγ agonist may be ROS-dependent, since they found that oxidized lipoproteins induced autophagy (Zabirnyk et al 2010). This suggestion was tested by studying a downstream protein of mammalian target of rapamycin (mTOR) pathway: p70S6 kinase. In P301S mice, levels of phospho-p70S6K were reduced after bezafibrate treatment, suggesting that the treatment could induce mTOR-dependent autophagy. In CHO cells transfected with 4R tau, troglitazone reduced tau phosphorylation, and the reduction was linked to a decrease of phospho-p70S6K levels (d'Abramo et al 2006). To confirm the autophagic activation, levels of LC3 were also assessed, since during autophagy, LC3 I (the cytoplasmic form of LC3) is recruited by autophagosomes and converted to LC3 II (the membrane bound form of LC3). It was observed that LC3 II was increased after treatment with bezafibrate, consistent with an induction of autophagy. It should be noted that with the current work, it cannot rule out the possible role of the proteasome system in the observed tau degradation. It has been previously shown that the protein tau can be degraded by the proteasome system (Yen 2011).

In addition to its action on tau, bezafibrate decreased inflammation in the brain by downregulating cyclooxygenase 2 (COX2). These data are consistent with previous reports showing that PPAR activation is critical to the anti-inflammatory response (Bernardo and Minghetti 2006; Kapadia et al 2008). In transgenic AD mice, pioglitazone reduced glial inflammation by decreasing levels of inducible nitric oxide synthase (iNOS) and COX2 (Heneka et al 2005). Oxidative stress markers in the brains of P301S mice were not elevated as compared to their wild-type littermates, but in the P301S mouse spinal cords, both nitrotyrosine and malondialdehyde were increased. Bezafibrate treatment reduced elevated nitrotyrosine and MDA levels to levels equivalent to those seen in wild-type mice.

The PPAR pathway is involved in energy metabolism (Wang 2010) and mitochondrial biogenesis (Alaynick 2008; Schrader and Fahimi 2006). The present data demonstrated that bezafibrate upregulated the PGC1α pathway by increasing expression of PGC1α, nuclear respiratory factor 1 (NRF1), and mitochondrial voltage-dependent anion channels (VDAC). Interestingly, similar effects were found in the brown adipose tissue. This tissue, which is used to generate body heat in mammals, contains small lipid droplets and a very high number of mitochondria (Richard and Picard 2011). During thermoregulation, uncoupling proteins allow the protons in the inter-membrane space of mitochondria to return to the mitochondrial matrix, leading to energy production and heat (Mozo et al 2005; Ricquier 2005). PPARs are known to be involved in this phenomenon (Villarroya et al 2007).

The importance of PGC1α as a co-activator is also crucial in the function of PPARs (Feige and Auwerx 2007; Fernandez-Marcos and Auwerx 2011), particularly in the brown adipose tissue (Uldry et al 2006), where it regulates expression of uncoupling protein 1 (UCP1). In a mouse model of mitochondrial myopathy caused by a loss of cytochrome oxidase subunit 10, activation of the PPAR/PGC1α pathway, by overexpression of PGC1α or by bezafibrate treatment, rescued mitochondrial abnormalities and delayed onset of the myopathy (Wenz et al 2008). On the other hand in another recent report, bezafibrate did not show beneficial effects in models of mitochondrial myopathy induced by Surf1, Sco2 and Cox15 deficiencies. The beneficial effects of bezafibrate may therefore be strain or subunit dependent in these models of myopathy (Viscomi et al 2011). In the present invention, it was observed that P301S mice had increased vacuolation of brown adipose tissue caused by downregulation of PGC1α gene expression, which may have caused a deficit in mitochondrial biogenesis. In P301S mice, PGC1α was localized at the periphery of very enlarged lipid droplets. After bezafibrate treatment, levels of PGC1α and its downstream targets were increased, which may have resulted in increased mitochondrial biogenesis and oxidation of fatty acids. After bezafibrate, PGC1α was diffuse in the cytoplasm of P301S mice, as seen in wild-type littermates (FIG. 17D), and this lead to the rescue of the brown fat pathology in P301S mice.

Therefore, the protective effects of the pan-PPAR agonist bezafibrate in P301S mice were present at various levels. In the brain, bezafibrate induced tau degradation and prevented tau phosphorylation. By downregulating microglia and COX2, bezafibrate also reduced inflammation. In the spinal cord and the brown adipose tissue, bezafibrate acted by inducing the PGC1α pathway and mitochondrial biogenesis, which reduced oxidative stress and brown fat vacuolation.

Data from initial clinical trials using specific PPAR agonists in AD were encouraging. The present invention for the first provides in vivo evidence that PPAR activation exerts beneficial effects and ameliorates the behavioral and neuropathologic effects of tauopathy. Thus, the use of potent pan-PPAR agonists may lead to improve efficacy in the treatment of neurodegenerative diseases.

ABBREVIATIONS

Peroxisome proliferator activated receptor (PPAR); Peroxisome proliferator activated receptor-γ-coactivator 1α (PGC-1α); Mitochondrial transcription factor a (Tfam); Cytochrome c (Cyt c); Nuclear respiratory factor-1 (NRF-1); Glutathione peroxidase-1 (Gpx-1); hemoxygenase-1 (HO-1), Nuclear factor (erythroid-derived 2)-like 2 (Nrf-2); Malondialdehyde (MDA); Brownadipose tissue (BAT).

REFERENCES

1. Abourbih, S., Filion, K. B., Joseph, L., Schiffrin, E. L., Rinfret, S., Poirier, P., Pilote, L., Genest, J., and Eisenberg, M. J. 2009. Effect of fibrates on lipid profiles and cardiovascular outcomes: a systematic review. Am J Med 122:962 e961-968.
2. Agarwal, R. and Chase, S. D. (2002) Rapid, fluorimetric-liquid chromatographic determination of malondialdehyde in biological samples. *J. Chromatogr. B Analyt. Technol. Biomed. Life Sci.,* 775, 121-126.
3. Alaynick, W. A. 2008. Nuclear receptors, mitochondria and lipid metabolism. Mitochondrion 8:329-337.
4. Andreassen, O. A., Dedeoglu, A., Ferrante, R. J., Jenkins, B. G., Ferrante, K. L., Thomas, M., Friedlich, A., Browne, S. E., Schilling, G., Borchelt, D. R. et al. (2001) Creatine increase survival and delays motor symptoms in a transgenic animal model of Huntington's disease. *Neurobiol. Dis.,* 8, 479-491.
5. Arrigoni, O., and Singer, T. P. 1962. Limitations of the phenazine methosulphate assay for succinic and related dehydrogenases. Nature 193:1256-1258.
6. Bahr, B. A. 2009. Lysosomal modulatory drugs for a broad strategy against protein accumulation disorders. Curr Alzheimer Res 6:438-445.
7. Bastin, J., Aubey, F., Rotig, A., Munnich, A. and Djouadi, F. (2008) Activation of peroxisome proliferator-activated receptor pathway stimulates the mitochondrial respiratory chain and can correct deficiencies in patients' cells lacking its components. *J. Clin. Endocrinol. Metab.,* 93, 1433-1441.
8. Beal, M. F. (1999) Mitochondria, NO and neurodegeneration. *Biochem. Soc. Symp.,* 66, 43-54.
9. Beal, M. F. and Ferrante, R. J. (2004) Experimental therapeutics in transgenic mouse models of Huntington's disease. *Nat. Rev. Neurosci.,* 5, 373-384.

10. Beal, M. F., Brouillet, E., Jenkins, B. G., Ferrante, R. J., Kowall, N. W., Miller, J. M., Storey, E., Srivastava, R., Rosen, B. R. and Hyman, B. T. (1993) Neurochemical and histologic characterization of striatal excitotoxic lesions produced by the mitochondrial toxin 3-nitropropionic acid. *J. Neurosci.,* 13, 4181-4192.

11. Bellucci, A., Westwood, A. J., Ingram, E., Casamenti, F., Goedert, M., and Spillantini, M. G. 2004. Induction of inflammatory mediators and microglial activation in mice transgenic for mutant human P301S tau protein. Am J Pathol 165:1643-1652.

12. Bensinger, S. J., and Tontonoz, P. 2008. Integration of metabolism and inflammation by lipid-activated nuclear receptors. Nature 454:470-477.

13. Berger J. and Moller D. E. (2002) The mechanisms of action of PPARs. Annu. Rev. Med. 53, 409-435.

14. Bernardo, A., and Minghetti, L. 2006. PPAR-gamma agonists as regulators of microglial activation and brain inflammation. Curr Pharm Des 12:93-109.

15. Besson, V. C., Chen, X. R., Plotkine, M., and Marchand-Verrecchia, C. 2005. Fenofibrate, a peroxisome proliferator-activated receptor alpha agonist, exerts neuroprotective effects in traumatic brain injury. Neurosci Lett 388: 7-12.

16. Bishop-Bailey D. (2000) Peroxisome proliferator-activated receptors in the cardiovascular system. Br. J. Pharmacol. 129, 823-834.

17. Brouillet, E., Hantraye, P., Ferrante, R. J., Dolan, R., Leroy-Willig, A., Kowall, N. W. and Beal, M. F. (1995) Chronic mitochondrial energy impairment produces selective striatal degeneration and abnormal choreiform movements in primates. *Proc. Natl. Acad. Sci. USA,* 92, 7105-7109.

18. Browne, S. E. and Beal, M. F. (2004) The energetics of Huntington's disease. *Neurochem. Res.,* 29, 531-546.

19. Browne, S. E. and Beal, M. F. (2006) Oxidative damage in Huntington's disease pathogenesis. *Antioxid. Redox Signal.,* 8, 2061-2073.

20. Browne, S. E., Bowling, A. C., MacGarvey, U., Balk, M. J., Berger, S. C., Muqit, M. M., Bird, E. D. and Beal, M. F. (1997) Oxidative damage and metabolic dysfunction in Huntington's disease: selective vulnerability of the basal ganglia. *Ann. Neurol.,* 41, 646-653.

21. Browne, S. E., Ferrante, R. J. and Beal, M. F. (1999) Oxidative stress in Huntington's disease. *Brain Pathol.,* 9, 147-163.

22. Buchan K. W. and Hassall D. G. (2000) PPAR agonists as direct modulators of the vessel wall in cardiovascular disease. Med. Res. Rev. 20, 350-366.

23. Cannon, B. and Nedergaard, J. (2004) Brown adipose tissue: function and physiological significance. *Physiol. Rev.,* 84, 277-359.

24. Casper D., Yaparpalvi U., Rempel N. and Werner P. (2000) Ibuprofen protects dopaminergic neurons against glutamate toxicity in vitro. Neurosci. Lett. 289, 201-204.

25. Castrillo A. and Tontonoz P. (2004) Nuclear receptors in macrophage biology: at the crossroads of lipid metabolism and inflammation. Annu. Rev. Cell Dev. Biol. 20, 455-480.

26. Chaturvedi, R. K., Adhihetty, P., Shukla, S., Hennessy, T., Calingasan, N., Yang, L., Starkov, A., Kiaei, M., Cannella, M., Sassone, J. et al. (2009) Impaired PGC-1alpha function in muscle in Huntington's disease. *Hum. Mol. Genet.,* 18, 3048-3065.

27. Chaturvedi, R. K., Calingasan, N. Y., Yang, L., Hennessey, T., Johri, A. and Beal, M. F. (2010) Impairment of PGC-1alpha expression, neuropathology and hepatic steatosis in a transgenic mouse model of Huntington's disease following chronic energy deprivation. *Hum. Mol. Genet.,* 19, 3190-3205.

28. Chen, X. R., Besson, V. C., Palmier, B., Garcia, Y., Plotkine, M., and Marchand-Leroux, C. 2007. Neurological recovery-promoting, anti-inflammatory, and anti-oxidative effects afforded by fenofibrate, a PPAR alpha agonist, in traumatic brain injury. J Neurotrauma 24:1119-1131.

29. Chiang, M. C., Chen, C. M., Lee, M. R., Chen, H. W., Chen, H. M., Wu, Y. S., Hung, C. H., Kang, J. J., Chang, C. P., Chang, C. et al. (2010) Modulation of energy deficiency in Huntington's disease via activation of the peroxisome proliferator-activated receptor gamma. *Hum. Mol. Genet.,* 19, 4043-58.

30. Cui, L., Jeong, H., Borovecki, F., Parkhurst, C. N., Tanese, N. and Krainc, D. (2006) Transcriptional repression of PGC-1alpha by mutant huntingtin leads to mitochondrial dysfunction and neurodegeneration. *Cell,* 127, 59-69.

31. Culman, J., Zhao, Y., Gohlke, P., and Herdegen, T. 2007. PPAR-gamma: therapeutic target for ischemic stroke. Trends Pharmacol Sci 28:244-249.

32. d'Abramo, C., Massone, S., Zingg, J. M., Pizzuti, A., Marambaud, P., Dalla Piccola, B., Azzi, A., Marinari, U. M., Pronzato, M. A., and Ricciarelli, R. 2005. Role of peroxisome proliferator-activated receptor gamma in amyloid precursor protein processing and amyloid beta-mediated cell death. Biochem J 391:693-698.

33. d'Abramo, C., Ricciarelli, R., Pronzato, M. A., and Davies, P. 2006. Troglitazone, a peroxisome proliferator-activated receptor-gamma agonist, decreases tau phosphorylation in CHOtau4R cells. J Neurochem 98:1068-1077.

34. Davies, S. W., Turmaine, M., Cozens, B. A., DiFiglia, M., Sharp, A. H., Ross, C. A., Scherzinger, E., Wanker, E. E., Mangiarini, L. and Bates, G. P. (1997) Formation of neuronal intranuclear inclusions underlies the neurological dysfunction in mice transgenic for the HD mutation. *Cell,* 90, 537-548.

35. Degli Esposti, M., Ghelli, A., Crimi, M., Estornell, E., Fato, R., and Lenaz, G. 1993. Complex I and complex III of mitochondria have common inhibitors acting as ubiquinone antagonists. Biochem Biophys Res Commun 190: 1090-1096.

36. Deplanque, D., Gele, P., Petrault, O., Six, I., Furman, C., Bouly, M., Nion, S., Dupuis, B., Leys, D., Fruchart, J. C., et al. 2003. Peroxisome proliferator-activated receptor-alpha activation as a mechanism of preventive neuroprotection induced by chronic fenofibrate treatment. J Neurosci 23:6264-6271.

37. Desvergne B. and Wahli W. (1999) Peroxisome proliferator-activated receptors: nuclear control of metabolism. Endocr. Rev. 20, 649-688.

38. Dill J et al. 2010. A molecular mechanism for ibuprofen-mediated RhoA inhibition in neurons. J Neurosci 30(3): 963-72.

39. Dumont, M., Wille, E., Calingasan, N. Y., Nathan, C., Flint Beal, M., and Lin, M. T. 2010 N-iminoethyl-L-lysine improves memory and reduces amyloid pathology in a transgenic mouse model of amyloid deposition. Neurochem Int 56:345-351.

40. Escribano, L., Simon, A. M., Perez-Mediavilla, A., Salazar-Colocho, P., Del Rio, J., and Frechilla, D. 2009. Rosiglitazone reverses memory decline and hippocampal 40. glucocorticoid receptor down-regulation in an Alzheimer's disease mouse model. Biochem Biophys Res Commun 379:406-410.
41. Feige, J. N., and Auwerx, J. 2007. Transcriptional coregulators in the control of energy homeostasis. Trends Cell Biol 17:292-301.
42. Fernandes-Santos, C., Carneiro, R. E., de Souza Mendonca, L., Aguila, M. B., and Mandarim-de-Lacerda, C. A. 2009. Pan-PPAR agonist beneficial effects in overweight mice fed a high-fat high-sucrose diet. Nutrition 25:818-827.
43. Fernandez-Marcos, P. J., and Auwerx, J. 2011. Regulation of PGC-1alpha, a nodal regulator of mitochondrial biogenesis. Am J Clin Nutr 93:884S-890.
44. Ferrante, R. J., Andreassen, O. A., Dedeoglu, A., Ferrante, K. L., Jenkins, B. G., Hersch, S. M. and Beal, M. F. (2002) Therapeutic effects of coenzyme Q10 and remacemide in transgenic mouse models of Huntington's disease. *J. Neurosci.*, 22, 1592-1599.
45. Ferrante, R. J., Ryu, H., Kubilus, J. K., D'Mello, S., Sugars, K. L., Lee, J., Lu, P., Smith, K., Browne, S., Beal, M. F. et al. (2004) Chemotherapy for the brain: the antitumor antibiotic mithramycin prolongs survival in a mouse model of Huntington's disease. *J. Neurosci.*, 24, 10335-10342.
46. Gizatullina, Z. Z., Lindenberg, K. S., Harjes, P., Chen, Y., Kosinski, C. M., Landwehrmeyer, B. G., Ludolph, A. C., Striggow, F., Zierz, S. and Gellerich, F. N. (2006) Low stability of Huntington muscle mitochondria against Ca2+ in R6/2 mice. *Ann. Neurol.*, 59, 407-411.
47. Gofflot F., Chartoire N., Vasseur L., Heikkinen S., Dembele D., Le Merrer J. and Auwerx J. (2007) Systematic gene expression mapping clusters nuclear receptors according to their function in the brain. Cell 131, 405-418.
48. Goldenberg, I., Benderly, M., and Goldbourt, U. 2008. Update on the use of fibrates: focus on bezafibrate. Vasc Health Risk Manag 4:131-141.
49. Gray, M., Shirasaki, D. I., Cepeda, C., Andre, V. M., Wilburn, B., Lu, X. H., Tao, J., Yamazaki, I., Li, S. H., Sun, Y. E. et al. (2008) Full-length human mutant huntingtin with a stable polyglutamine repeat can elicit progressive and selective neuropathogenesis in BACHD mice. *J. Neurosci.*, 28, 6182-6195.
50. Hayden, M. R. and Kremer, B. (2001) Huntington Disease. In Scriver, C., Beaudet, A., Sly, W. and Valle, D. (eds.), *The Metabolic and Molecular Basis of Inherited Disease*. McGraw-Hill, New York, USA, 8th edn., pp. 5677-5701.
51. Hedreen, J. C. and Folstein, S. E. (1995) Early loss of neostriatal striosome neurons in Huntington's disease. *J. Neuropathol. Exp. Neurol.*, 54, 105-120.
52. Heneka M. T., Landreth G. E. and Hull M. (2007) Drug insight: effects mediated by peroxisome proliferator-activated receptor-gamma in CNS disorders. Nat. Clin. Pract. Neurol. 3, 496-504.
53. Heneka, M. T., and Landreth, G. E. 2007. PPARs in the brain. Biochim Biophys Acta 1771:1031-1045.
54. Heneka, M. T., Sastre, M., Dumitrescu-Ozimek, L., Hanke, A., Dewachter, I., Kuiperi, C., O'Banion, K., Klockgether, T., Van Leuven, F., and Landreth, G. E. 2005. Acute treatment with the PPARgamma agonist pioglitazone and ibuprofen reduces glial inflammation and Abetal-42 levels in APPV717I transgenic mice. Brain 128:1442-1453.
55. Hernandez, F., de Barreda, E. G., Fuster-Matanzo, A., Goni-Oliver, P., Lucas, J. J., and Avila, J. 2009. The role of GSK3 in Alzheimer disease. Brain Res Bull 80:248-250.
56. Hersch, S. M. and Ferrante, R. J. (2004) Translating therapies for Huntington's disease from genetic animal models to clinical trials. *NeuroRx*, 1, 298-306.
57. Hersch, S. M., Gevorkian, S., Marder, K., Moskowitz, C., Feigin, A., Cox, M., Como, P., Zimmerman, C., Lin, M., Zhang, L. et al. (2006) Creatine in Huntington disease is safe, tolerable, bioavailable in brain and reduces serum 8OH2'dG. *Neurology*, 66, 250-252.
58. Hinerfeld, D., Traini, M. D., Weinberger, R. P., Cochran, B., Doctrow, S. R., Harry, J. and Melov, S. (2004) Endogenous mitochondrial oxidative stress: neurodegeneration, proteomic analysis, specific respiratory chain defects, and efficacious antioxidant therapy in superoxide dismutase 2 null mice. *J. Neurochem.*, 88, 657-667.
59. Ho, D. J., Calingasan, N. Y., Wille, E., Dumont, M. and Beal, M. F. (2010) Resveratrol protects against peripheral deficits in a mouse model of Huntington's disease. *Exp. Neurol.*, 225, 74-84.
60. Hondares, E., Mora, O., Yubero, P., Rodriguez de la Concepcion, M., Iglesias, R., Giralt, M. and Villarroya, F. (2006) Thiazolidinediones and rexinoids induce peroxisome proliferator-activated receptor-coactivator (PGC)-1alpha gene transcription: an autoregulatory loop controls PGC-1alpha expression in adipocytes via peroxisome proliferator-activated receptor-gamma coactivation. *Endocrinology*, 147, 2829-2838.
61. Huss, J. M. and Kelly, D. P. (2004) Nuclear receptor signaling and cardiac energetics. *Circ. Res.*, 95, 568-578.
62. Jiang, C., Ting A. T. and Seed B. (1998) PPAR-gamma agonists inhibit production of monocyte inflammatory cytokines. Nature 391, 82-86.
63. Jiang, Q., Heneka, M., and Landreth, G. E. 2008. The role of peroxisome proliferator-activated receptor-gamma (PPARgamma) in Alzheimer's disease: therapeutic implications. CNS Drugs 22:1-14.
64. Kamei Y., Xu L., Heinzel T. et al. (1996) A CBP integrator complex mediates transcriptional activation and AP-1 inhibition by nuclear receptors. Cell 85, 403-414.
65. Kapadia, R., Yi, J. H., and Vemuganti, R. 2008. Mechanisms of anti-inflammatory and neuroprotective actions of PPAR-gamma agonists. Front Biosci 13:1813-1826.
66. Kaundal, R. K., and Sharma, S. S. 2010. Peroxisome proliferator-activated receptor gamma agonists as neuroprotective agents. Drug News Perspect 23:241-256.
67. Kersten, S., Desvergne, B., and Wahli, W. 2000. Roles of PPARs in health and disease. Nature 405:421-424.
68. Khurana, V., Elson-Schwab, I., Fulga, T. A., Sharp, K. A., Loewen, C. A., Mulkearns, E., Tyynela, J., Scherzer, C. R., and Feany, M. B. 2010. Lysosomal dysfunction promotes cleavage and neurotoxicity of tau in vivo. PLoS Genet 6:e1001026.
69. Kiaei, M., Kipiani, K., Chen, J., Calingasan, N. Y., and Beal, M. F. 2005. Peroxisome proliferator-activated receptor-gamma agonist extends survival in transgenic mouse model of amyotrophic lateral sclerosis. Exp Neurol 191:331-336.
70. Kim, J., Moody, J. P., Edgerly, C. K., Bordiuk, O. L., Cormier, K., Smith, K., Beal, M. F. and Ferrante, R. J. (2010) Mitochondrial loss, dysfunction and altered dynamics in Huntington's disease. *Hum. Mol. Genet.*, 19, 3919-3935.

71. Kosinski, C. M., Schlangen, C., Gellerich, F. N., Gizatullina, Z., Deschauer, M., Schiefer, J., Young, A. B., Landwehrmeyer, G. B., Toyka, K. V., Sellhaus, B. et al. (2007) Myopathy as a first symptom of Huntington's disease in a Marathon runner. *Mov. Disord.,* 22, 1637-1640.
72. Kreisler, A., Duhamel, A., Vanbesien-Mailliot, C., Destee, A., and Bordet, R. 2010. Differing short-term neuroprotective effects of the fibrates fenofibrate and bezafibrate in MPTP and 6-OHDA experimental models of Parkinson's disease. Behav Pharmacol 21:194-205.
73. Lagouge, M., Argmann, C., Gerhart-Hines, Z., Meziane, H., Lerin, C., Daussin, F., Messadeq, N., Milne, J., Lambert, P., Elliott, P. et al. (2006) Resveratrol improves mitochondrial function and protects against metabolic disease by activating SIRT1 and PGC-1alpha. *Cell,* 127, 1109-1122.
74. Landreth, G. 2007. Therapeutic use of agonists of the nuclear receptor PPARgamma in Alzheimer's disease. Curr Alzheimer Res 4:159-164.
75. Lehmann J. M., Lenhard J. M., Oliver 8. B., Ringold G. M. and Kliewer S. A. (1997) Peroxisome proliferator-activated receptors alpha and gamma are activated by indomethacin and other non-steroidal antiinflammatory drugs. J. Biol. Chem. 272, 3406-3410.
76. Leone, T. C., Lehman, J. J., Finck, B. N., Schaeffer, P. J., Wende, A. R., Boudina, S., Courtois, M., Wozniak, D. F., Sambandam, N., Bernal-Mizrachi, C. et al. (2005) PGC-1alpha deficiency causes multi-system energy metabolic derangements: muscle dysfunction, abnormal weight control and hepatic steatosis. *PLoS Biol.,* 3, e101.
77. Lin, J., Handschin, C. and Spiegelman, B. M. (2005) Metabolic control through the PGC-1 family of transcription coactivators. *Cell Metab.,* 1, 361-370.
78. Lin, J., Wu, H., Tarr, P. T., Zhang, C. Y., Wu, Z., Boss, O., Michael, L. F., Puigserver, P., Isotani, E., Olson, E. N. et al. (2002) Transcriptional co-activator PGC-1 alpha drives the formation of slow-twitch muscle fibres. *Nature,* 418, 797-801.
79. Lin, J., Wu, P. H., Tarr, P. T., Lindenberg, K. S., St-Pierre, J., Zhang, C. Y., Mootha, V. K., Jager, S., Vianna, C. R., Reznick, R. M. et al. (2004) Defects in adaptive energy metabolism with CNS-linked hyperactivity in PGC-1alpha null mice. *Cell,* 119, 121-135.
80. Mangiarini, L., Sathasivam, K., Seller, M., Cozens, B., Harper, A., Hetherington, C., Lawton, M., Trottier, Y., Lehrach, H., Davies, S. W. et al. (1996) Exon 1 of the HD gene with an expanded CAG repeat is sufficient to cause a progressive neurological phenotype in transgenic mice. *Cell,* 87, 493-506.
81. Menalled, L., El-Khodor, B. F., Patry, M., Suarez-Farinas, M., Orenstein, S. J., Zahasky, B., Leahy, C., Wheeler, V., Yang, X. W., MacDonald, M. et al. (2009) Systematic behavioral evaluation of Huntington's disease transgenic and knock-in mouse models. *Neurobiol. Dis.,* 35, 319-336.
82. Menalled, L. B. and Chesselet, M. F. (2002) Mouse models of Huntington's disease. *Trends Pharmacol. Sci.,* 23, 32-39.
83. Mozo, J., Emre, Y., Bouillaud, F., Ricquier, D., and Criscuolo, F. 2005. Thermoregulation: what role for UCPs in mammals and birds? Biosci Rep 25:227249.
84. Munigoti, S. P., and Rees, A. 2011. Evidence for use of fibrates in diabetic dyslipidemia: are we looking hard enough? Curr Opin Lipidol 22:76-77.
85. Nicolakakis, N., Aboulkassim, T., Ongali, B., Lecrux, C., Fernandes, P., Rosa-Neto, P., Tong, X. K., and Hamel, E. 2008. Complete rescue of cerebrovascular function in aged Alzheimer's disease transgenic mice by antioxidants and pioglitazone, a peroxisome proliferator-activated receptor gamma agonist. J Neurosci 28:9287-9296.
86. Nicolakakis, N., and Hamel, E. 2010. The Nuclear Receptor PPARgamma as a Therapeutic Target for Cerebrovascular and Brain Dysfunction in Alzheimer's Disease. Front Aging Neurosci 2.
87. Nolte R. T., Wisely G. 8., Westin S., Cobb J. E., Lambert M. H., Kurokawa R., Rosenfeld M. G., Willson T. M., Glass C. K. and Milburn M. V. (1998) Ligand binding and co-activator assembly of the peroxisome proliferator-activated receptor-gamma. Nature 395, 137-143.
88. Okamoto, S., Pouladi, M. A., Talantova, M., Yao, D., Xia, P., Ehrnhoefer, D. E., Zaidi, R., Clemente, A., Kaul, M., Graham, R. K. et al. (2009) Balance between synaptic versus extrasynaptic NMDA receptor activity influences inclusions and neurotoxicity of mutant huntingtin. *Nat. Med.,* 15, 1407-1413.
89. Phan, J., Hickey, M. A., Zhang, P., Chesselet, M. F. and Reue, K. (2009) Adipose tissue dysfunction tracks disease progression in two Huntington's disease mouse models. *Hum. Mol. Genet.,* 18, 1006-1016.
90. Plattner, F., Angelo, M., and Giese, K. P. 2006. The roles of cyclin-dependent kinase 5 and glycogen synthase kinase 3 in tau hyperphosphorylation. J Biol Chem 281:25457-25465.
91. Puigserver, P., Wu, Z., Park, C. W., Graves, R., Wright, M. and Spiegelman, B. M. (1998) A cold-inducible coactivator of nuclear receptors linked to adaptive thermogenesis. *Cell,* 92, 829-839.
92. Qi c., Zhu Y. and Reddy J. K. (2000) Peroxisome proliferator-activated receptors, coactivators, and downstream targets. Cell Biochem. Biophys. 32, 187-204.
93. Quintanilla, R. A., Jin, Y. N., Fuenzalida, K., Bronfman, M. and Johnson, G. V. (2008) Rosiglitazone treatment prevents mitochondrial dysfunction in mutant huntingtin-expressing cells: possible role of peroxisome proliferator-activated receptor-gamma (PPARgamma) in the pathogenesis of Huntington disease. *J. Biol. Chem.,* 283, 25628-25637.
94. Rakhshandehroo, M., Knoch, B., Muller, M., and Kersten, S. 2010. Peroxisome proliferator-activated receptor alpha target genes. PPAR Res 2010.
95. Richard, D., and Picard, F. 2011. Brown fat biology and thermogenesis. Front Biosci 16:1233-1260.
96. Ricote M., Li A. c., Willson T. M., Kelly C. J. and Glass C. K. (1998) The peroxisome proliferator-activated receptor-gamma is a negative regulator of macrophage activation. Nature 391, 79-82.
97. Ricquier, D. 2005. Respiration uncoupling and metabolism in the control of energy expenditure. Proc Nutr Soc 64:47-52.
98. Santos, M. J., Quintanilla, R. A., Toro, A., Grandy, R., Dinamarca, M. C., Godoy, J. A., and Inestrosa, N. C. 2005. Peroxisomal proliferation protects from beta-amyloid neurodegeneration. J Biol Chem 280:41057-41068.
99. Scattoni, M. L., Gasparini, L., Alleva, E., Goedert, M., Calamandrei, G., and Spillantini, M. G. 2010. Early behavioural markers of disease in P301S tau transgenic mice. Behav Brain Res 208:250-257.
100. Schrader, M., and Fahimi, H. D. 2006. Peroxisomes and oxidative stress. Biochim Biophys Acta 1763:1755-1766.
101. Schulman, I. G. 2010. Nuclear receptors as drug targets for metabolic disease. Adv Drug Deliv Rev 62:1307-1315.

102. Soutar, M. P., Kim, W. Y., Williamson, R., Peggie, M., Hastie, C. J., McLauchlan, H., Snider, W. D., Gordon-Weeks, P. R., and Sutherland, C. 2010. Evidence that glycogen synthase kinase-3 isoforms have distinct substrate preference in the brain. J Neurochem 115:974-983.

103. Srere, P. A. 1969. Citrate synthase. In Methods in Enzymology. 3-11.

104. Stack, C., Ho, D., Wille, E., Calingasan, N. Y., Williams, C., Liby, K., Sporn, M., Dumont, M. and Beal, M. F. (2010) Triterpenoids CDDO-ethyl amide and CDDO-trifluoroethyl amide improve the behavioral phenotype and brain pathology in a transgenic mouse model of Huntington's disease. *Free Radic. Biol. Med.,* 49, 147-158.

105. Stack, E. C., Matson, W. R. and Ferrante, R. J. (2008) Evidence of oxidant damage in Huntington's disease: translational strategies using antioxidants. *Ann. N. Y Acad. Sci.,* 1147, 79-92.

106. Staels B. The clinical significance of PPARα and g agonism. Br J Diabetes Vasc Dis 2002; 2(suppl 1):528-531.

107. Staels, B., Maes, M., and Zambon, A. 2008. Fibrates and future PPARαalpha agonists in the treatment of cardiovascular disease. Nat Clin Pract Cardiovasc Med 5:542-553.

108. Stoy, N., Mackay, G. M., Forrest, C. M., Christofides, J., Egerton, M., Stone, T. W. and Darlington, L. G. (2005) Tryptophan metabolism and oxidative stress in patients with Huntington's disease. *J. Neurochem.,* 93, 611-623.

109. St-Pierre, J., Drori, S., Uldry, M., Silvaggi, J. M., Rhee, J., Jager, S., Handschin, C., Zheng, K., Lin, J., Yang, W. et al. (2006) Suppression of reactive oxygen species and neurodegeneration by the PGC-1 transcriptional coactivators. Cell, 127, 397-408.

110. Straus D. S. and Glass C. K. (2001) Cyclopentenone prostaglandins: new insights on biological activities and cellular targets. Med. Res. Rev. 21, 185-210.

111. Straus D. S. and Glass C. K. (2007) Anti-inflammatory actions of PPAR ligands: new insights on cellular and molecular mechanisms. Trends Immunol. 28, 551-558.

112. Strum, J. C., Shehee, R., Virley, D., Richardson, J., Mattie, M., Selley, P., Ghosh, S., Nock, C., Saunders, A., and Roses, A. 2007. Rosiglitazone induces mitochondrial biogenesis in mouse brain. J Alzheimers Dis 11:45-51.

113. Taherzadeh-Fard, E., S aft, C., Andrich, J., Wieczorek, S. and Arning, L. (2009) PGC-1alpha as modifier of onset age in Huntington disease. *Mol. Neurodegener.,* 4, 10.

114. Tenenbaum, A., Motro, M. and Fisman, E. Z. (2005) Dual and pan-peroxisome proliferator-activated receptors (PPAR) co-agonism: the bezafibrate lessons. *Cardiovasc. Diabetol.,* 4, 14.

115. Turner, C., Cooper, J. M. and Schapira, A. H. (2007) Clinical correlates of mitochondrial function in Huntington's disease muscle. *Mov. Disord.,* 22, 1715-1721.

116. Uldry, M., Yang, W., St-Pierre, J., Lin, J., Seale, P., and Spiegelman, B. M. 2006. Complementary action of the PGC-1 coactivators in mitochondrial biogenesis and brown fat differentiation. Cell Metab 3:333-341.

117. van Neerven S, Mey J. (2007). RARjRXR and PPAR-jRXR Signaling in Spinal Cord Injury. PPAR Res. 2007: 29275.

118. Villarroya, F., Iglesias, R., and Giralt, M. 2007. PPARs in the Control of Uncoupling Proteins Gene Expression. PPAR Res 2007:74364.

119. Viscomi, C., Bottani, E., Civiletto, G., Cerutti, R., Moggio, M., Fagiolari, G., Schon, E. A., Lamperti, C., and Zeviani, M. 2011. In Vivo Correction of COX Deficiency by Activation of the AMPK/PGC-1alpha Axis. Cell Metab 14:80-90.

120. Vonsattel, J. P. and DiFiglia, M. (1998) Huntington disease. *J. Neuropathol. Exp. Neurol.,* 57, 369-384.

121. Wang, Y. X. 2010. PPARs: diverse regulators in energy metabolism and metabolic diseases. Cell Res 20:124-137.

122. Wareski, P., Vaarmann, A., Choubey, V., Safiulina, D., Liiv, J., Kuum, M. and Kaasik, A. (2009) PGC-1{alpha} and PGC-1{beta} regulate mitochondrial density in neurons. *J. Biol. Chem.,* 284, 21379-21385.

123. Wenz, T., Diaz, F., Spiegelman, B. M. and Moraes, C. T. (2008) Activation of the PPAR/PGC-1alpha pathway prevents a bioenergetic deficit and effectively improves a mitochondrial myopathy phenotype. *Cell Metab.,* 8, 249-256.

124. Wenz, T., Wang, X., Marini, M., and Moraes, C. T. (Dec. 3, 2010). A metabolic shift induced by a PPAR panagonist markedly reduces the effects of pathogenic mitochondrial tRNA mutations. *J. Cell. Mol. Med.,* 10.1111/j.1582-4934.2010.01223.x.

125. Weydt, P., Pineda, V. V., Torrence, A. E., Libby, R. T., Satterfield, T. F., Lazarowski, E. R., Gilbert, M. L., Morton, G. J., Bammler, T. K., Strand, A. D. et al. (2006) Thermoregulatory and metabolic defects in Huntington's disease transgenic mice implicate PGC-1alpha in Huntington's disease neurodegeneration. *Cell Metab.,* 4, 349-362.

126. Weydt, P., Soyal, S. M., Gellera, C., Didonato, S., Weidinger, C., Oberkofler, H., Landwehrmeyer, G. B. and Patsch, W. (2009) The gene coding for PGC-1alpha modifies age at onset in Huntington's Disease. Mol. Neurodegener., 4, 3.

127. Xiang, Z., Valenza, M., Cui, L., Leoni, V., Jeong, H. K., Brilli, E., Zhang, J., Peng, Q., Duan, W., Reeves, S. A. et al. (2011) Peroxisome-Proliferator-Activated Receptor Gamma Coactivator 1 {alpha} Contributes to Dysmyelination in Experimental Models of Huntington's Disease. *J. Neurosci.,* 31, 9544-9553.

128. Yen, S. S. 2011. Proteasome degradation of brain cytosolic tau in Alzheimer's disease. Int J Clin Exp Pathol 4:385-402.

129. Yoshiyama, Y., Higuchi, M., Zhang, B., Huang, S. M., Iwata, N., Saido, T. C., Maeda, J., Suhara, T., Trojanowski, J. Q., and Lee, V. M. 2007. Synapse loss and microglial activation precede tangles in a P301S tauopathy mouse model. Neuron 53:337-351.

130. Yu, Z. X., Li, S. H., Evans, J., Pillarisetti, A., Li, H. and Li, X. J. (2003) Mutant huntingtin causes context-dependent neurodegeneration in mice with Huntington's disease. *J. Neurosci.,* 23, 2193-2202.

131. Zabirnyk, O., Liu, W., Khalil, S., Sharma, A., and Phang, J. M. 2010. Oxidized low-density lipoproteins upregulate proline oxidase to initiate ROS-dependent autophagy. Carcinogenesis 31:446-454.

132. Zhou, J., Zhang, W., Liang, B., Casimiro, M. C., Whitaker-Menezes, D., Wang, M., Lisanti, M. P., Lanza-Jacoby, S., Pestell, R. G., and Wang, C. 2009. PPAR-gamma activation induces autophagy in breast cancer cells. Int J Biochem Cell Biol 41:2334-2342.

133. Ziouzenkova O. and Plutzky J. (2008) Retinoid metabolism and nuclear receptor responses: new insights into coordinated regulation of the PPAR-RXR complex. FEBS Lett. 582, 32-38.

134. Zuccato, C., Valenza, M. and Cattaneo, E. (2010) Molecular mechanisms and potential therapeutical targets in Huntington's disease. *Physiol. Rev.,* 90, 905-981.

The invention claimed is:

1. A method for treating a tauopathy comprising administering to a subject in need a therapeutic composition comprising an effective amount of bezafibrate, wherein the tauopathy is a member of Pick's complex.

2. The method of claim 1, wherein the method is for treating the tauopathy.

3. The method of claim 1, wherein the member of Pick's complex is Progressive supranuclear palsy; Dementia pugilistica (chronic traumatic encephalopathy); traumatic encephalopathy; Frontotemporal dementia and parkinsonism linked to chromosome 17; Lytico-Bodig disease (Parkinson-dementia complex of Guam); Tangle-predominant dementia; Ganglioglioma; gangliocytoma; Meningioangiomatosis; Subacute sclerosing panencephalitis; lead encephalopathy; tuberous sclerosis; Hallervorden-Spatz disease; lipofuscinosis; Pick's disease; corticobasal degeneration; Argyrophilic grain disease (AGD); corticobasal degeneration; Frontotemporal dementia; or Frontotemporal lobar degeneration.

4. The method of claim 1, wherein the therapeutic composition further comprises a pharmaceutically acceptable carrier or excipient for a suitable formulation and administration.

5. The method of claim 4, wherein the therapeutic composition is administered orally.

6. The method of claim 4, wherein the therapeutic composition is administered intravenously, intramuscularly, or via a suitable parental administration route.

7. The method of claim 4, wherein the therapeutic composition is formulated for controlled-release.

8. The method of claim 4, wherein the therapeutic composition is formulated for sustained-release.

9. The method of claim 1, wherein the therapeutic composition is administered in conjunction with another therapeutic agent before, during, or after the administration of the bezafibrate.

* * * * *

UNITED STATES PATENT AND TRADEMARK OFFICE
CERTIFICATE OF CORRECTION

| | | |
|---|---|---|
| PATENT NO. | : 9,592,212 B2 | Page 1 of 1 |
| APPLICATION NO. | : 14/274025 | |
| DATED | : March 14, 2017 | |
| INVENTOR(S) | : Flint Beal | |

It is certified that error appears in the above-identified patent and that said Letters Patent is hereby corrected as shown below:

In the Specification

At Column 1, Line 16, delete "Grant Numbers P01AG14930 and" and insert --grant number--.

At Column 1, Lines 17-18, delete "United States Government" and insert --government--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*